United States Patent
Jacobs et al.

(12) 
(10) Patent No.: US 6,365,686 B1
(45) Date of Patent: Apr. 2, 2002

(54) METHOD FOR PRODUCING A CYCLOOLEFIN COPOLYMER

(75) Inventors: Alexandra Jacobs, Niedernhausen; Gerhard Fink, Mülheim an der Ruhr; Dieter Ruchatz, Hasselroth, all of (DE)

(73) Assignee: Ticona GmbH (DE)

( * ) Notice: Subject to any disclaimer, the term of this patent is extended or adjusted under 35 U.S.C. 154(b) by 0 days.

(21) Appl. No.: 09/331,333

(22) PCT Filed: Dec. 16, 1997

(86) PCT No.: PCT/EP97/07043

§ 371 Date: Jul. 29, 1999

§ 102(e) Date: Jul. 29, 1999

(87) PCT Pub. No.: WO98/27125

PCT Pub. Date: Jun. 25, 1998

(30) Foreign Application Priority Data

Dec. 17, 1996 (DE) .......................................... 196 52 338

(51) Int. Cl.$^7$ ........................... C08F 4/16; C08F 212/04
(52) U.S. Cl. ...................... 526/127; 526/160; 526/161; 526/943; 526/280; 526/281; 502/152; 502/155
(58) Field of Search ................................. 526/160, 161, 526/281, 943, 335, 336, 339, 348.6, 127, 280; 502/152, 155

(56) References Cited

U.S. PATENT DOCUMENTS 5,635,573 A    6/1997    Harrington et al. ......... 526/170

FOREIGN PATENT DOCUMENTS

EP           0 671 404 A2 *    9/1995
WO           WO 9640806         12/1996

* cited by examiner

*Primary Examiner*—David W. Wu
*Assistant Examiner*—R. Harlan
(74) *Attorney, Agent, or Firm*—Connolly Bove Lodge & Hutz LLP

(57) ABSTRACT

The invention relates to a method for producing a cycloolefin copolymer by polymerization of 0.1–99.9 wt. %, with respect to the total amount of monomers, of at least one polycyclic olefin, 0–99.9 wt. %, with respect to the total amount of monomers, of at least one monocyclic olefin, 0.1–99.9 wt. %, with respect to the total amount of monomers, of at least one acyclic 1-olefin, in the presence of a catalyst system consisting of at least one cocatalyst and at least one metal coordination complex with taut geometry.

24 Claims, No Drawings

METHOD FOR PRODUCING A CYCLOOLEFIN COPOLYMER

The invention relates to a process for preparing cycloolefin copolymers having high molar masses.

It is known from the literature that cycloolefin homopolymers and copolymers can be prepared using metallocene-aluminoxane catalyst systems (EP-A-283 164, EP-A-407 870). The polymerization of the cycloolefins proceeds here with retention of the rings and can be carried out in solvents or in bulk. As solvents, it is possible to use hydrocarbons.

Cycloolefin copolymers can be prepared with a high cycloolefin content and then have a high glass transition temperature. This is associated with a high heat distortion resistance, which is why these polymers are suitable for use as thermoplastic molding compositions. Cycloolefin copolymers having a low cycloolefin content have a low glass transition temperature. At use temperature, they have a high ductility and can have elastomeric properties.

It is found that cycloolefin copolymers prepared by means of metallocene technology have a relatively low mass average molar mass. In addition, the use of ethylene as comonomer frequently results in formation of partially crystalline ethylene polymers as by-products which can significantly impair the transparency of the cycloolefin copolymers.

It is an object of the present invention to provide a process for preparing cycloolefin copolymers having a relatively high mass average molar mass together with high transparency.

The object of the present invention has been achieved by a process for preparing a cycloolefin copolymer by polymerization of from 0.1 to 99.9% by weight, based on the total amount of monomers, of at least one polycyclic olefin, from 0 to 99.9% by weight, based on the total amount of monomers, of at least one monocyclic olefin and from 0.1 to 99.9% by weight, based on the total amount of monomers, of at least one acyclic 1-olefin in the presence of a catalyst system.

The polymerization is carried out in the liquid cycloolefin itself or in cycloolefin solution, with the pressure advantageously being above 1 bar.

The catalyst system to be used in the process of the invention comprises at least one metal complex comprising a metal of groups 3 to 10 or of the lanthanide series of the Periodic Table of the Elements and a conjugated π system coordinated to the metal. The conjugated z system coordinated to the metal may be substituted by a group which is likewise coordinated to the metal atom and results in the strained geometry of the metal complex. Comparable structures are described in EP-A-416 815, in EP-A-418 044 and in EP-A-698 618.

The metal complex to be used in the process of the invention is preferably a compound of the formula (I)

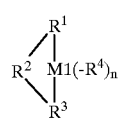

(I)

where
M¹ is a metal of groups 3 to 10 or of the lanthanide series of the Periodic Table of the Elements,
R¹ is a delocalized acyclic π system such as $C_4$–$C_{20}$-alkenyl, $C_4$–$C_{20}$-alkynyl, $C_3$–$C_{20}$-allyl, $C_4$–$C_{20}$-alkadienyl, $C_4$–$C_{20}$-polyenyl or a comparable structure which may comprise up to 5 hetero atoms, or an unsubstituted or substituted delocalized $C_5$–$C_{40}$-cyclic π system or a comparable structure which may comprise up to 5 hetero atoms, R² is a single- or multi-membered bridge which links the radicals R¹ and R³ and comprises at least one atom of group 14 of the Periodic Table of the Elements or at least one boron atom and may comprise one or more sulfur or oxygen atoms and can form a fused ring system together with R¹, R³ is an anionic or nonionic ligand which is coordinated to M¹ and comprises one or more nitrogen, phosphorus, oxygen and/or sulfur atoms and can form a fused ring system together with R², and R⁴ is an anionic or nonionic ligand, where n=0, 1, 2, 3 or 4 depending on the valence of M.

The catalyst system to be used in the process of the invention can further comprise one or more cocatalysts.

The catalyst system to be used in the process of the invention is a highly active catalyst for olefin polymerization. Preference is given to using one metal complex and one cocatalyst. It is also possible to use mixtures of two or more metal complexes, particularly for preparing reactor blends or polyolefins having a broad or multimodal molar mass distribution.

Preference is given to a metal complex comprising a metal of group 4 or the lanthanide series of the Periodic Table of the Elements. Preference is also given to a metal complex which comprises a delocalized cyclic $\eta^5$-coordinated π system. Preference is given to delocalized cyclic π systems such as cyclopentadienyl, indenyl, fluorenyl or substituted cyclopentadienyl, substituted indenyl or substituted fluorenyl or comparable structures which may comprise up to 5 hetero atoms. Here, one or more of the atoms of the delocalized cyclic π system may be substituted, in which case the substituents may be identical or different and may comprise, in addition to hydrogen, atoms of group 14 of the Periodic Table of the Elements and/or one or more hetero atoms such as those of groups 15, 16 and 17 of the Periodic Table of the Elements. Two or more of the substituents can form a ring. Examples of substituted delocalized cyclic π systems are methylcyclopentadienyl, ethylcyclopentadienyl, isopropylcyclopentadienyl, t-butylcyclopentadienyl, dimethylcyclopentadienyi, diethylcyclopentadienyl, diisopropylcyclopentadienyl, di-t-butylcyclopentadienyl and tetramethylcyclopentadienyl.

The metal complex to be used in the process of the invention is particularly preferably a compound of the formula (Ia)

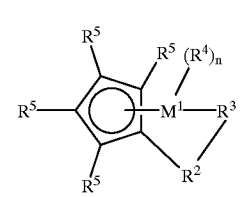

(Ia)

in which
M¹ is a metal of group 4 or the lanthanide series of the Periodic Table of the Elements,
R² is a single- or multi-membered bridge which links the $\eta^5$-coordinated cyclic π system and R and is preferably

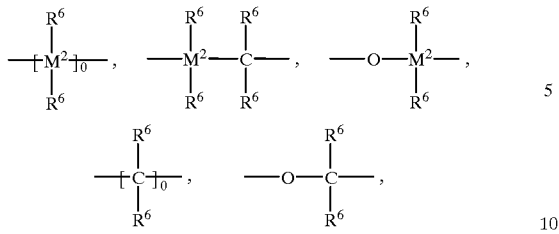

=BR$^6$, =AlR, —Ge—, —Sn—, —O—, —S—, =SO, =SO$_2$, =NR, =CO, =PR$^6$ or =P(O)R$^6$, where R$^6$ are identical or different and are each a hydrogen atom, a halogen atom, a C$_1$–C$_{40}$-group such as a C$_1$–C$_{10}$-alkyl group which may be halogenated, a C$_6$–C$_{20}$-aryl group which may be halogenated, a C$_6$–C$_{20}$-aryloxy group, a C$_2$–C$_{12}$-alkenyl group, a C$_7$–C$_{40}$-arylalkyl group, a C$_7$–C$_{40}$-alkylaryl group, a C$_8$–C$_{40}$-arylalkenyl group, —SiR$^7{}_3$, —NR$^7{}_2$, —Si(OR$^7$)$_3$, —Si(SR$^7$)$_3$ or —PR$^7{}_2$, where R$^7$ are identical or different and are each a halogen atom, a C$_1$–C$_{10}$-alkyl group or a C$_6$–C$_{10}$-aryl group or form a ring system, where o≧1, and M$^2$ is silicon, germanium or tin, R$^3$ is O, S, NR$^8$, PR$^8$ or an uncharged 2-electron donor ligand selected from the group consisting of OR$^8$, SR$^8$, NR$^8{}_2$, PR$^8{}_2$, where R$^8$ is a hydrogen atom, a halogen atom, a C$_1$–C$_{40}$-group such as a C$_1$–C$_8$-alkyl group which may be halogenated, a C$_6$–C$_{20}$-aryl group which may be halogenated, a C$_6$–C$_{20}$-aryloxy group, a C$_2$–C$_{12}$-alkenyl group, a C$_7$–C$_{40}$-arylalkyl group, a C$_7$–C$_{40}$-alkylaryl group, a C$_8$–C$_{40}$-arylalkenyl group, —SiR$^9{}_3$, —NR$^9{}_2$, —Si(OR$^9$)$_3$, —Si(SR$^9$)$_3$ or —PR$^9{}_2$, where R$^9$ are identical or different and are each a halogen atom, a C$_1$–C$_{10}$-alkyl group or a C$_6$–C$_{10}$-aryl group, R$^4$ are identical or different and are each a hydrogen atom, a C$_1$–C$_{40}$-group such as a C$_1$–C$_{10}$-alkyl group, a C$_1$–C$_{10}$-alkoxy group, a C$_6$–C$_{10}$-aryl group, a C$_6$–C$_{25}$-aryloxy group, a C$_2$–C$_{10}$-alkenyl group, a C$_7$–C$_{40}$-arylalkyl group or a C$_7$–C$_{40}$-arylalkenyl group, an OH group, a halogen atom or NR$^{10}{}_2$, where R$^{10}$ is a halogen atom, a C$_1$–C$_{10}$-alkyl group or a C$_6$–C$_{10}$-aryl group, or R$^4$ together with the atoms connecting them form a ring system, where n=1 or 2, R$^5$ are identical or different and are each a hydrogen atom, a halogen atom, a C$_1$–C$_{40}$-group such as a C$_1$–C$_{10}$-alkyl group which may be halogenated, a C$_6$–C$_{20}$-aryl group which may be halogenated, a C$_6$–C$_{20}$-aryloxy group, a C$_2$–C$_{12}$-alkenyl group, a C$_7$–C$_{40}$-arylalkyl group, a C$_7$–C$_{40}$-alkylaryl group or a C$_8$–C$_{40}$-arylalkenyl group, —SiR$^{11}{}_3$, —NR$^{11}{}_2$, —Si(OR$^{11}$)$_3$, —Si(SR$^{11}$)$_3$ or —PR$^{11}{}_2$, where R$^{11}$ are identical or different and are each a halogen atom, a C$_1$–C$_{10}$-alkyl group or a C$_6$–C$_{10}$-aryl group or form a ring system, or two or more adjacent substituents R together with the atoms connecting them form a ring system which preferably comprises from 4 to 40, particularly preferably from 6 to 20, carbon atoms.

The metal complex to be used in the process of the invention is particularly preferably a compound of the formula (Ib):

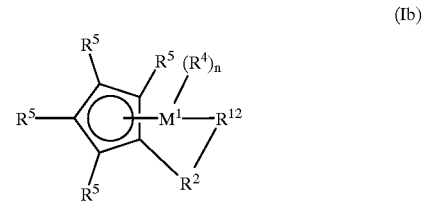

(Ib)

where

M$^1$ is titanium,

R$^2$ is a single-, two- or three-membered bridge which links the η$^5$-coordinated cyclic π system and R$^3$ and is preferably

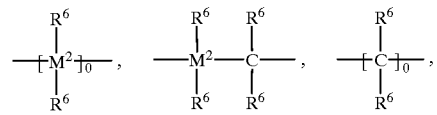

where R$^6$ are identical or different and are each a hydrogen atom, a C$_1$–C$_{40}$-group such as a C$_1$–C$_{10}$-alkyl group which may be halogenated, a C$_6$–C$_{20}$-aryl group which may be halogenated, a C$_6$–C$_{20}$-aryloxy group, a C$_2$–C$_{12}$-alkenyl group, a C$_7$–C$_{40}$-arylalkyl group, a C$_7$–C$_{40}$-alkylaryl group or a C$_8$–C$_{40}$-arylalkenyl group, where o=1, 2 or 3, and M$^2$ is silicon, R$^3$ is NR$^8$, where R$^8$ is a hydrogen atom, a C$_1$–C$_{40}$-group such as a C$_1$–C$_8$-alkyl group which may be halogenated, a C$_1$–C$_{10}$-alkoxy group, a C$_6$–C$_{20}$-aryl group which may be halogenated, a C$_6$–C$_{20}$-aryloxy group, a C$_2$–C$_{12}$-alkenyl group, a C$_7$–C$_{40}$-arylalkyl group, a C$_7$–C$_{40}$-alkylaryl group or a C$_8$–C$_{40}$-arylalkenyl group, R$^4$ are identical or different and are each a hydrogen atom, a C$_1$–C$_{40}$-group such as a C$_1$–C$_{10}$-alkyl group, a C$_1$–C$_{10}$-alkoxy group, a C$_6$–C$_{10}$-aryl group, a C$_6$–C$_{25}$-aryloxy group, a C$_2$–C$_{10}$-alkenyl group, a C$_7$–C$_{40}$-arylalkyl group or a C$_7$–C$_{40}$-arylalkenyl group, an OH group, a halogen atom or NR$^{10}{}_2$, where R$^{10}$ is a halogen atom, a C$_1$–C$_{10}$-alkyl group or a C$_6$–C$_{10}$-aryl group, or together with the atoms connecting them form a ring system, R$^5$ are identical or different and are each a hydrogen atom, a C$_1$–C$_{10}$-alkyl group or trimethylsilyl group or two of the substituents R$^5$ together with the cyclopentadienyl system connecting them form a six-membered aromatic fused ring.

Examples of metal complexes to be used according to the invention are:

(methylamido)(η$^5$-cyclopentadienyl) dimethylsilanezirconium dichloride (methylamido)(η$^5$-cyclopentadienyl) dimethylsilanezirconium bis(diethylamide)

(ethylamido)(η$^5$-cyclopentadienyl) dimethylsilanezirconium dichloride (ethylamido)(η$^5$-cyclopentadienyl) dimethylsilanezirconium bis(diethylamide)

(isopropylamido)(η$^5$-cyclopentadienyl) dimethylsilanezirconium dichloride (isopropylamido)(η$^5$-cyclopentadienyl) dimethylsilanezirconium bis(diethylamide)

(t-butylamido)(η⁵-cyclopentadienyl) dimethylsilanezirconium dichloride
(t-butylamido)(η⁵-cyclopentadienyl) dimethylsilanezirconium bis(diethylamide)
(phenylamido)(η⁵-cyclopentadienyl) dimethylsilanezirconium dichloride
(phenylamido)(η⁵-cyclopentadienyl) dimethylsilanezirconium bis(diethylamide)
(cyclohexylamido)(η⁵-cyclopentadienyl) dimethylsilanezirconium dichloride
(cyclohexylamido)(η⁵-cyclopentadienyl) dimethylsilanezirconium bis(diethylamide)
(methylamido)(η⁵-cyclopentadienyl) dimethylsilanetitanium dichloride
(methylamido)(η⁵-cyclopentadienyl) dimethylsilanetitanium dibromide
(methylamido)(η⁵-cyclopentadienyl) dimethylsilanetitanium bis(dimethylamide)
(methylamido)(η⁵-cyclopentadienyl) dimethylsilanetitanium bis(diethylamide)
(ethylamido)(η⁵-cyclopentadienyl) dimethylsilanetitanium dichloride
(ethylamido)(η⁵-cyclopentadienyl) dimethylsilanetitanium dibromide
(ethylamido)(η⁵-cyclopentadienyl) dimethylsilanetitanium bis(dimethylamide)
(ethylamido)(η⁵-cyclopentadienyl) dimethylsilanetitanium bis(diethylamide)
(isopropylamido)(η⁵-cyclopentadienyl) dimethylsilanetitanium dichloride
(isopropylamido)(η⁵-cyclopentadienyl) dimethylsilanetitanium dibromide
(isopropylamido)(η⁵-cyclopentadienyl) dimethylsilanetitanium bis(dimethylamide)
(isopropylamido)(η⁵-cyclopentadienyl) dimethylsilanetitanium bis(diethylamide)
(t-butylamido)(η⁵-cyclopentadienyl) dimethylsilanetitanium dichloride
(t-butylamido)(η⁵-cyclopentadienyl) dimethylsilanetitanium dibromide
(t-butylamido)(η⁵-cyclopentadienyl) dimethyisilanetitanium bis(dimethylamide)
(t-butylamido)(η⁵-cyclopentadienyl) dimethylsilanetitanium bis(diethylamide)
(phenylamido)(η⁵-cyclopentadienyl) dimethylsilanetitanium dichloride
(phenylamido)(η⁵-cyclopentadienyl) dimethylsilanetitanium dibromide
(phenylamido)(η⁵-cyclopentadienyl) dimethylsilanetitanium bis(dimethylamide)
(phenylamido)(η⁵-cyclopentadienyl) dimethylsilanetitanium bis(diethylamide)
(cyclohexylamido)(η⁵-cyclopentadienyl) dimethylsilanetitanium dichloride
(cyclohexylamido)(η⁵-cyclopentadienyl) dimethylsilanetitanium dibromide
(cyclohexylamido)(η⁵-cyclopentadienyl) dimethylsilanetitanium bis(dimethylamide)
(cyclohexylamido)(η⁵-cyclopentadienyl) dimethylsilanetitanium bis(diethylamide)
(methylamido)(3-methyl-η⁵-cyclopentadienyl) dimethylsilanezirconium dichloride
(methylamido)(3-methyl-η⁵-cyclopentadienyl) dimethylsilanezirconium bis(diethylamide)
(ethylamido)(3-methyl-η⁵-cyclopentadienyl) dimethylsilanezirconium dichloride
(ethylamido)(3-methyl-η⁵-cyclopentadienyl) dimethylsilanezirconium bis(dimethylamide
(isopropylamido)(3-methyl-η⁵-cyclopentadienyl) dimethylsilanezirconium dichloride
(isopropylamido)(3-methyl-η⁵-cyclopentadienyl) dimethylsilanezirconium bis(diethylamide)
(t-butylamido)(3-methyl-η⁵-cyclopentadienyl) dimethylsilanezirconium dichloride
(t-butylamido)(3-methyl-η⁵-cyclopentadienyl) dimethylsilanezirconium bis(diethylamide)
(phenylamido)(3-methyl-η⁵-cyclopentadienyl) dimethylsilanezirconium dichloride
(phenylamido)(3-methyl-η⁵-cyclopentadienyl) dimethylsilanezirconium bis(diethylamide)
(cyclohexylamido)(3-methyl-η⁵-cyclopentadienyl) dimethylsilanezirconium dichloride
(cyclohexylamido)(3-methyl-η⁵-cyclopentadienyl) dimethylsilanezirconium bis(diethylamide)
(methylamido)(3-methyl-η⁵-cyclopentadienyl) dimethylsilanetitanium dichloride
(methylamido)(3-methyl-η⁵-cyclopentadienyl) dimethylsilanetitanium dibromide
(methylamido)(3-methyl-η⁵-cyclopentadienyl) dimethylsilanetitanium bis(dimethylamide)
(methylamido)(3-methyl-η⁵-cyclopentadienyl) dimethylsilanetitanium bis(diethylamide)
(ethylamido)(3-methyl-η⁵-cyclopentadienyl) dimethylsilanetitanium dichloride
(ethylamido)(3-methyl-η⁵-cyclopentadienyl) dimethylsilanetitanium dibromide
(ethylamido)(3-methyl-η⁵-cyclopentadienyl) dimethylsilanetitanium bis(dimethylamide)
(ethylamido)(3-methyl-η⁵-cyclopentadienyl) dimethylsilanetitanium bis(diethylamide)
(isopropylamido)(3-methyl-η⁵-cyclopentadienyl) dimethylsilanetitanium dichloride
(isopropylamido)(3-methyl-η⁵-cyclopentadienyl) dimethylsilanetitanium dibromide
(isopropylamido)(3-methyl-η⁵-cyclopentadienyl) dimethylsilanetitanium bis(dimethylamide)
(isopropylamido)(3-methyl-η⁵-cyclopentadienyl) dimethylsilanetitanium bis(diethylamide)
(t-butylamido)(3-methyl-η⁵-cyclopentadienyl) dimethylsilanetitanium dichloride
(t-butylamido)(3-methyl-η⁵-cyclopentadienyl) dimethylsilanetitanium dibromide
(t-butylamido)(3-methyl-η⁵-cyclopentadienyl) dimethylsilanetitanium bis(dimethylamide)
(t-butylamido)(3-methyl-η⁵-cyclopentadienyl) dimethylsilanetitanium bis(diethylamide)
(phenylamido)(3-methyl-η⁵-cyclopentadienyl) dimethylsilanetitanium dichloride
(phenylamido)(3-methyl-η⁵-cyclopentadienyl) dimethylsilanetitanium dibromide
(phenylamido)(3-methyl-η⁵-cyclopentadienyl) dimethylsilanetitanium bis(dimethylamide)
(phenylamido)(3-methyl-η⁵-cyclopentadienyl) dimethylsilanetitanium bis(diethylamide (cyclohexylamido)(3-methyl-η⁵-cyclopentadienyl) dimethylsilanetitanium dichloride
(cyclohexylamido)(3-methyl-η⁵-cyclopentadienyl) dimethylsilanetitanium dibromide
(cyclohexylamido)(3-methyl-η⁵-cyclopentadienyl) dimethylsilanetitanium bis(dimethylamide)
(cyclohexylamido)(3-methyl-η⁵-cyclopentadienyl) dimethylsilanetitanium bis(diethylamide)
(methylamido)(3-ethyl-η⁵-cyclopentadienyl) dimethylsilanezirconium dichloride
(methylamido)(3-ethyl-η⁵-cyclopentadienyl) dimethylsilanezirconium bis(diethylamide)
(ethylamido)(3-ethyl-η⁵-cyclopentadienyl) dimethylsilanezirconium dichloride
(ethylamido)(3-ethyl-η⁵-cyclopentadienyl) dimethylsilanezirconium bis(diethylamide)
(isopropylamido)(3-ethyl-η⁵-cyclopentadienyl) dimethylsilanezirconium dichloride
(isopropylamido)(3-ethyl-η⁵-cyclopentadienyl) dimethylsilanezirconium bis(diethylamide)
(t-butylamido)(3-ethyl-η⁵-cyclopentadienyl) dimethylsilanezirconium dichloride
(t-butylamido)(3-ethyl-η⁵-cyclopentadienyl) dimethylsilanezirconium bis(diethylamide)
(phenylamido)(3-ethyl-η⁵-cyclopentadienyl) dimethylsilanezirconium dichloride
(phenylamido)(3-ethyl-η⁵-cyclopentadienyl) dimethylsilanezirconium bis(diethylamide)
(cyclohexylamido)(3-methyl-η⁵-cyclopentadienyl) dimethylsilanezirconium dichloride
(cyclohexylamido)(3-ethyl-η⁵-cyclopentadienyl) dimethylsilanezirconium bis(diethylamide)
(methylamido)(3-ethyl-η⁵-cyclopentadienyl) dimethylsilanetitanium dichloride
(methylamido)(3-ethyl-η⁵-cyclopentadienyl) dimethylsilanetitanium dibromide
(methylamido)(3-ethyl-η⁵-cyclopentadienyl) dimethylsilanetitanium bis(dimethylamide)
(methylamido)(3-ethyl-η⁵-cyclopentadienyl) dimethylsilanetitanium bis(diethylamide)
(ethylamido)(3-ethyl-η⁵-cyclopentadienyl) dimethylsilanetitanium dichloride
(ethylamido)(3-ethyl-η⁵-cyclopentadienyl) dimethylsilanetitanium dibromide
(ethylamido)(3-ethyl-η⁵-cyclopentadienyl) dimethylsilanetitanium bis(dimethylamide)
(ethylamido)(3-ethyl-η⁵-cyclopentadienyl) dimethylsilanetitanium bis(diethylamide)
(isopropylamido)(3-ethyl-η⁵-cyclopentadienyl) dimethylsilanetitanium dichloride
(isopropylamido)(3-ethyl-η⁵-cyclopentadienyl) dimethylsilanetitanium dibromide
(isopropylamido)(3-ethyl-η⁵-cyclopentadienyl) dimethylsilanetitanium bis(dimethylamide)
(isopropylamido)(3-ethyl-η⁵-cyclopentadienyl) dimethylsilanetitanium bis(diethylamide)
(t-butylamido)(3-ethyl-η⁵-cyclopentadienyl) dimethylsilanetitanium dichloride
(t-butylamido)(3-ethyl-η⁵-cyclopentadienyl) dimethylsilanetitanium dibromide
(t-butylamido)(3-ethyl-η⁵-cyclopentadienyl) dimethylsilanetitanium bis(dimethylamide)
(t-butylamido)(3-ethyl-η⁵-cyclopentadienyl) dimethylsilanetitanium bis(diethylamide)
(phenylamido)(3-ethyl-η⁵-cyclopentadienyl) dimethylsilanetitanium dichloride
(phenylamido)(3-ethyl-η⁵-cyclopentadienyl) dimethylsilanetitanium dibromide
(phenylamido)(3-ethyl-η⁵-cyclopentadienyl) dimethylsilanetitanium bis(dimethylamide)
(phenylamido)(3-ethyl-η⁵-cyclopentadienyl) dimethylsilanetitanium bis(diethylamide)
(cyclohexylamido)(3-methyl-η⁵-cyclopentadienyl) dimethylsilanetitanium dichloride
(cyclohexylamido)(3-ethyl-η⁵-cyclopentadienyl) dimethylsilanetitanium dibromide
(cyclohexylamido)(3-ethyl-η⁵-cyclopentadienyl) dimethylsilanetitanium bis(dimethylamide)
(cyclohexylamido)(3-ethyl-η⁵-cyclopentadienyl) dimethylsilanetitanium bis(diethylamide)
(methylamido)(tetramethyl-η⁵-cyclopentadienyl) dimethylsilanezirconium dichloride
(methylamido)(tetramethyl-η⁵-cyclopentadienyl) dimethylsilanezirconium bis(diethylamide)
(ethylamido)d(tetramethyl-η⁵-cyclopentadienyl) dimethylsilanezirconium dichloride
(ethylamido)(tetramethyl-η⁵-cyclopentadienyl) dimethylsilanezirconium bis(diethylamide)
(isopropylamido)(tetramethyl-η⁵-cyclopentadienyl) dimethylsilanezirconium dichloride
(isopropylamido)(tetramethyl-η⁵-cyclopentadienyl) dimethylsilanezirconium bis(diethylamide)
(t-butylamido)(tetramethyl-η⁵-cyclopentadienyl) dimethylsilanezirconium dichloride
(t-butylamido)(tetramethyl-η⁵-cyclopentadienyl) dimethylsilanezirconium bis(diethylamide)
(phenylamido)(tetramethyl-η⁵-cyclopentadienyl) dimethylsilanezirconium dichloride
(phenylamido)(tetramethyl-η⁵-cyclopentadienyl) dimethylsilanezirconium bis(diethylamide)
(cyclohexylamido)(tetramethyl-η⁵-cyclopentadienyl) dimethylsilanezirconium dichloride
(cyclohexylamido)(tetramethyl-η⁵-cyclopentadienyl) dimethylsilanezirconium bis(diethylamide)
(methylamido)(tetramethyl-η⁵-cyclopentadienyl) dimethylsilanetitanium dichloride
(methylamido)(tetramethyl-η⁵-cyclopentadienyl) dimethylsilanetitanium dibromide
(methylamido)(tetramethyl-η⁵-cyclopentadienyl) dimethylsilanetitanium bis(dimethylamide)
(methylamido)(tetramethyl-η⁵-cyclopentadienyl) dimethylsilanetitanium bis(diethylamide)
(ethylamido)(tetramethyl-η⁵-cyclopentadienyl) dimethylsilanetitanium dichloride
(ethylamido)(tetramethyl-η⁵-cyclopentadienyl) dimethylsilanetitanium dibromide
(ethylamido)(tetramethyl-η⁵-cyclopentadienyl) dimethylsilanetitanium bis(dimethylamide)
(ethylamido)(tetramethyl-η⁵-cyclopentadienyl) dimethylsilanetitanium bis(diethylamide)
(isopropylamido)(tetramethyl-η⁵-cyclopentadienyl) dimethylsilanetitanium dichloride
(isopropylamido)(tetramethyl-η⁵-cyclopentadienyl) dimethylsilanetitanium dibromide (isopropylamido)(tetramethyl-η⁵-cyclopentadienyl) dimethylsilanetitanium bis(dimethylamide)
(isopropylamido)(tetramethyl-η⁵-cyclopentadienyl) dimethylsilanetitanium bis(diethylamide)
(t-butylamido)(tetramethyl-η⁵-cyclopentadienyl) dimethylsilanetitanium dichloride
(t-butylamido)(tetramethyl-η⁵-cyclopentadienyl) dimethylsilanetitanium dibromide
(t-butylamido)(tetramethyl-η⁵-cyclopentadienyl) dimethyisilanetitanium bis(dimethylamide)
(t-butylamido)(tetramethyl-η⁵-cyclopentadienyl) dimethylsilanetitanium bis(diethylamide)
(phenylamido)(tetramethyl-η⁵-cyclopentadienyl) dimethylsilanetitanium dichloride
(phenylamido)(tetramethyl-η⁵-cyclopentadienyl) dimethylsilanetitanium dibromide
(phenylamido)(tetramethyl-η⁵-cyclopentadienyl) dimethylsilanetitanium bis(dimethylamide)
(phenylamido)(tetramethyl-η⁵-cyclopentadienyl) dimethylsilanetitanium bis(diethylamide)
(cyclohexylamido)(tetramethyl-η⁵-cyclopentadienyl) dimethylsilanetitanium dichloride
(cyclohexylamido)(tetramethyl-η⁵-cyclopentadienyl) dimethylsilanetitanium dibromide
(cyclohexylamido)(tetramethyl-η⁵-cyclopentadienyl) dimethylsilanetitanium bis(dimethylamide)
(cyclohexylamido)(tetramethyl-η⁵-cyclopentadienyl) dimethylsilanetitanium bis(diethylamide)
(methylamido)(1-η⁵-indenyl)dimethylsilanezirconium dichloride
(methylamido)(1-η⁵-indenyl)dimethylsilanezirconium bis(diethylamide)
(ethylamido)(1-η⁵-indenyl)dimethylsilanezirconium dichloride
(ethylamido)(1-η⁵-indenyl)dimethylsilanezirconium bis(diethylamide)
(isopropylamido)(1-η⁵-indenyl)dimethylsilanezirconium dichloride
(isopropylamido)(1-η⁵-indenyl)dimethylsilanezirconium bis(diethylamide)
(t-butylamido)(1-η⁵-indenyl)dimethylsilanezirconium dichloride
(t-butylamido)(1-η⁵-indenyl)dimethylsilanezirconium bis(diethylamide)
(phenylamido)(1-η⁵-indenyl)dimethylsilanezirconium dichloride
(phenylamido)(1-η⁵-indenyl)dimethylsilanezirconium bis(diethylamide)
(cyclohexylamido)(1-η⁵-indenyl) dimethylsilanezirconium dichloride
(cyclohexylamido)(1-η⁵-indenyl) dimethylsilanezirconium bis(diethylamide
(methylamido)(1-η⁵-indenyl)dimethylsilanetitanium dichloride
(methylamido)(1-η⁵-indenyl)dimethylsilanetitanium dibromide
(methylamido)(1-η⁵-indenyl)dimethylsilanetitanium bis(dimethylamide)
(methylamido)(1-η⁵-indenyl)dimethylsilanetitanium bis(diethylamide)
(ethylamido)(1-η⁵-indenyl)dimethylsilanetitanium dichloride
(ethylamido)(1-η⁵-indenyl)dimethylsilanetitanium dibromide
(ethylamido)(1-η⁵-indenyl)dimethylsilanetitanium bis(dimethylamide)
(ethylamido)(1-η⁵-indenyl)dimethylsilanetitanium bis(diethylamide)
(isopropylamido)(1-η⁵-indenyl)dimethylsilanetitanium dichloride
(isopropylamido)(1-η⁵-indenyl)dimethylsilanetitanium dibromide
(isopropylamido)(1-η⁵-indenyl)dimethylsilanetitanium bis(dimethylamide)
(isopropylamido)(1-η⁵-indenyl)dimethylsilanetitanium bis(diethylamide)
(t-butylamido)(1-η⁵-indenyl)dimethylsilanetitanium dichloride
(t-butylamido)(1-η⁵-indenyl)dimethylsilanetitanium dibromide
(t-butylamido)(1-η⁵-indenyl)dimethylsilanetitanium bis(dimethylamide)
(t-butylamido)(1-η⁵-indenyl)dimethylsilanetitanium bis(diethylamide)
(phenylamido)(1-η⁵-indenyl)dimethylsilanetitanium dichloride
(phenylamido)(1-η⁵-indenyl)dimethyisilanetitanium dibromide
(phenylamido)(1-η⁵-indenyl)dimethylsilanetitanium bis(dimethylamide)
(phenylamido)(1-η⁵-indenyl)dimethylsilanetitanium bis(diethylamide)
(cyclohexylamido)(1-η⁵-indenyl)dimethylsilanetitanium dichloride
(cyclohexylamido)(1-η⁵-indenyl)dimethylsilanetitanium dibromide
(cyclohexylamido)(1-η⁵-indenyl)dimethylsilanetitanium bis(dimethylamide)
(cyclohexylamido)(1-η⁵-indenyl)dimethylsilanetitanium bis(diethylamide)
(methylamido)(9-η⁵-fluorenyl)dimethylsilanezirconium dichloride
(methylamido)(9-η⁵-fluorenyl)dimethylsilanezirconium bis(diethylamide)
(ethylamido)(9-η⁵-fluorenyl)dimethylsilanezirconium dichloride
(ethylamido)(9-η⁵-fluorenyl)dimethylsilanezirconium bis(diethylamide)
(isopropylamido)(9-η⁵-fluorenyl) dimethylsilanezirconium dichloride
(isopropylamido)(9-η⁵-fluorenyl) dimethylsilanezirconium bis(diethylamide)
(t-butylamido)(9-η⁵-fluorenyl)dimethylsilanezirconium dichloride
(t-butylamido)(9-η⁵-fluorenyl)dimethylsilanezirconium bis(diethylamide)
(phenylamido)(9-η⁵-fluorenyl)dimethylsilanezirconium dichloride
(phenylamido)(9-η⁵-fluorenyl)dimethylsilanezirconium bis(dimethylamide)
(cyclohexylamido)(9-η⁵-fluorenyl) dimethylsilanezirconium dichloride
(cyclohexylamido)(9-η⁵-fluorenyl) dimethylsilanezirconium bis(diethylamide)

(methylamido)(9-η⁵-fluorenyl)dimethylsilanetitanium dichloride
(methylamido)(9-η⁵-fluorenyl)dimethylsilanetitanium dibromide
(methylamido)(9-η⁵-fluorenyl)dimethylsilanetitanium bis(dimethylamide)
(methylamido)(9-η⁵-fluorenyl)dimethylsilanetitanium bis(diethylamide)
(ethylamido)(9-η⁵-fluorenyl)dimethylsilanetitanium dichloride
(ethylamido)(9-η⁵-fluorenyl)dimethylsilanetitanium dibromide
(ethylamido)(9-η⁵-fluorenyl)dimethylsilanetitanium bis(dimethylamide)
(ethylamido)(9-η⁵-fluorenyl)dimethylsilanetitanium bis(diethylamide)
(isopropylamido)(9-η⁵-fluorenyl)dimethylsilanetitanium dichloride
(isopropylamido)(9-η⁵-fluorenyl)dimethylsilanetitanium dibromide
(isopropylamido)(9-η⁵-fluorenyl)dimethylsilanetitanium bis(dimethylamide)
(isopropylamido)(9-η⁵-fluorenyl)dimethylsilanetitanium bis(diethylamide)
(t-butylamido)(9-η⁵-fluorenyl)dimethylsilanetitanium dichloride
(t-butylamido)(9-η⁵-fluorenyl)dimethyisilanetitanium dibromide
(t-butylamido)(9-η⁵-fluorenyl)dimethylsilanetitanium bis(dimethylamide)
(t-butylamido)(9-η⁵-fluorenyl)dimethylsilanetitanium bis(diethylamide)
(phenylamido)(9-η⁵-fluorenyl)dimethylsilanetitanium dichloride
(phenylamido)(9-η⁵-fluorenyl)dimethylsilanetitanium dibromide
(phenylamido)(9-η⁵-fluorenyl)dimethylsilanetitanium bis(dimethylamide)
(phenylamido)(9-η⁵-fluorenyl)dimethylsilanetitanium bis(diethylamide)
(cyclohexylamido)(9-η⁵-fluorenyl)dimethylsilanetitanium dichloride
(cyclohexylamido)(9-η⁵-fluorenyl)dimethylsilanetitanium dibromide
(cyclohexylamido)(9-η⁵-fluorenyl)dimethylsilanetitanium bis(dimethylamide)
(cyclohexylamido)(9-η⁵-fluorenyl)dimethylsilanetitanium bis(diethylamide)
1-(methylamido)-2-(η⁵-cyclopentadienyl)ethanediylzirconium dichloride
1-(methylamido)-2-(η⁵-cyclopentadienyl)ethanediylzirconium bis(diethylamide)
1-(ethylamido)-2-(η⁵-cyclopentadienyl)ethanediylzirconium dichloride
1-(ethylamido)-2-(η⁵-cyclopentadienyl)ethanediyldimehtylsilanezirconium bis(diethylamide)
1-(isopropylamido)-2-(η⁵-cyclopentadienyl)ethanediylzirconium dichloride
1-(isopropylamido)-2-(η⁵-cyclopentadienyl)ethanediylzirconium bis(diethylamide)
1-(t-butylamido)-2-(η⁵-cyclopentadienyl)ethanediylzirconium dichloride
1-(t-butylamido)-2-(η⁵-cyclopentadienyl)ethanediylzirconium bis(diethylamide)
1-(phenylamido)-2-(η⁵-cyclopentadienyl)ethanediylzirconium dichloride
1-(phenylamido)-2-(η⁵-cyclopentadienyl)ethanediylzirconium bis(diethylamide)
1-(cyclohexylamido)-2-(η⁵-cyclopentadienyl)ethanediylzirconium dichloride
1-(cyclohexylamido)-2-(η⁵-cyclopentadienyl)ethanediylzirconium bis(diethylamide)
1-(methylamido)-2-(η⁵-cyclopentadienyl)ethanediyltitanium dichloride
1-(methylamido)-2-(η⁵-cyclopentadienyl)ethanediyltitanium dibromide
1-(methylamido)-2-(η⁵-cyclopentadienyl)ethanediyltitanium bis(dimethylamide)
1-(methylamido)-2-(η⁵-cyclopentadienyl)ethanediyltitanium bis(diethylamide)
1-(ethylamido)-2-(η⁵-cyclopentadienyl)ethanediyltitanium dichloride
1-(ethylamido)-2-(η⁵-cyclopentadienyl)ethanediyltitanium dibromide
1-(ethylamido)-2-(η⁵-cyclopentadienyl)ethanediyltitanium bis(dimethylamide)
1-(ethylamido)-2-(η⁵-cyclopentadienyl)ethanediyltitanium bis(diethylamide)
1-(isopropylamido)-2-(η⁵-cyclopentadienyl)ethanediyltitanium dichloride
1-(isopropylamido)-2-(η⁵-cyclopentadienyl)ethanediyltitanium dibromide
1-(isopropylamido)-2-(η⁵-cyclopentadienyl)ethanediyltitanium bis(dimethylamide)
1-(isopropylamido)-2-(η⁵-cyclopentadienyl)ethanediyltitanium bis(diethylamide)
1-(t-butylamido)-2-(η⁵-cyclopentadienyl)ethanediyltitanium dichloride
1-(t-butylamido)-2-(η⁵-cyclopentadienyl)ethanediyltitanium dibromide
1-(t-butylamido)-2-(η⁵-cyclopentadienyl)ethanediyltitanium bis(dimethylamide)
1-(t-butylamido)-2-(η⁵-cyclopentadienyl)ethanediyltitanium bis(diethylamide)
1-(phenylamido)-2-(η⁵-cyclopentadienyl)ethanediyltitanium dichloride
1-(phenylamido)-2-(η⁵-cyclopentadienyl)ethanediyltitanium dibromide
1-(phenylamido)-2-(η⁵-cyclopentadienyl)ethanediyltitanium bis(dimethylamide)
1-(phenylamido)-2-(η⁵-cyclopentadienyl)ethanediyltitanium bis(diethylamide)
1-(cyclohexylamido)-2-(η⁵-cyclopentadienyl)ethanediyltitanium dichloride
1-(cyclohexylamido)-2-(η⁵-cyclopentadienyl)ethanediyltitanium dibromide
1-(cyclohexylamido)-2-(η⁵-cyclopentadienyl)ethanediyltitanium bis(dimethylamide)
1-(cyclohexylamido)-2-(η⁵-cyclopentadienyl)ethanediyltitanium bis(diethylamide)
1-(methylamido)-2-(3-methyl-η⁵-cyclopentadienyl)ethanediylzirconium dichloride
1-(methylamido)-2-(3-methyl-η⁵-cyclopentadienyl)ethanediylzirconium bis(diethylamide)

1-(ethylamido)-2-(3-methyl-η⁵-cyclopentadienyl)
  ethanediylzirconium dichloride
1-(ethylamido)-2-(3-methyl-η⁵-cyclopentadienyl)
  ethanediylzirconium bis(diethylamide)
1-(isopropylamido)-2-(3-methyl-η⁵-cyclopentadienyl)
  ethanediylzirconium dichloride
1-(isopropylamido)-2-(3-methyl-η⁵-cyclopentadienyl)
  ethanediylzirconium bis(diethylamide)
1-(t-butylamido)-2-(3-methyl-η⁵-cyclopentadienyl)
  ethanediylzirconium dichloride
1-(t-butylamido)-2-(3-methyl-η⁵-cyclopentadienyl)
  ethanediylzirconium bis(diethylamide)
1-(phenylamido)-2-(3-methyl-η⁵-cyclopentadienyl)
  ethanediylzirconium dichloride
1-(phenylamido)-2-(3-methyl-η⁵-cyclopentadienyl)
  ethanediylzirconium bis(diethylamide)
1-(cyclohexylamido)-2-(3-methyl-η⁵-cyclopentadienyl)
  ethanediylzirconium dichloride
1-(cyclohexylamido)-2-(3-methyl-η⁵-cyclopentadienyl)
  ethanediylzirconium bis(diethylamide)
1-(methylamido)-2-(3-methyl-η⁵-cyclopentadienyl)
  ethanediyltitanium dichloride
1-(methylamido)-2-(3-methyl-η⁵-cyclopentadienyl)
  ethanediyltitanium dibromide
1-(methylamido)-2-(3-methyl-η⁵-cyclopentadienyl)
  ethanediyltitanium bis(dimethylamide)
1-(methylamido)-2-(3-methyl-η⁵-cyclopentadienyl)
  ethanediyltitanium bis(diethylamide)
1-(ethylamido)-2-(3-methyl-η⁵-cyclopentadienyl)
  ethanediyltitanium dichloride
1-(ethylamido)-2-(3-methyl-η⁵-cyclopentadienyl)
  ethanediyltitanium dibromide
1-(ethylamido)-2-(3-methyl-η⁵-cyclopentadienyl)
  ethanediyltitanium bis(dimethylamide)
1-(ethylamido)-2-(3-methyl-η⁵-cyclopentadienyl)
  ethanediyltitanium bis(dimethylamide)
1-(isopropylamido)-2-(3-methyl-η⁵-cyclopentadienyl)
  ethanediyltitanium dichloride
1-(isopropylamido)-2-(3-methyl-η⁵-cyclopentadienyl)
  ethanediyltitanium dibromide
1-(isopropylamido)-2-(3-methyl-η⁵-cyclopentadienyl)
  ethanediyltitanium bis(dimethylamide)
1-(isopropylamido)-2-(3-methyl-η⁵-cyclopentadienyl)
  ethanediyltitanium bis(diethylamide)
1-(t-butylamido)-2-(3-methyl-η⁵-cyclopentadienyl)
  ethanediyltitanium dichloride
1-(t-butylamido)-2-(3-methyl-η⁵-cyclopentadienyl)
  ethanediyltitanium dibromide
1-(t-butylamido)-2-(3-methyl-η⁵-cyclopentadienyl)
  ethanediyltitanium bis(dimethylamide)
1-(t-butylamido)-2-(3-methyl-η⁵-cyclopentadienyl)
  ethanediyltitanium bis(diethylamide)
1-(phenylamido)-2-(3-methyl-η⁵-cyclopentadienyl)
  ethanediyltitanium dichloride
1-(phenylamido)-2-(3-methyl-η⁵-cyclopentadienyl)
  ethanediyltitanium dibromide
1-(phenylamido)-2-(3-methyl-η⁵-cyclopentadienyl)
  ethanediyltitanium bis(dimethylamide)
1-(phenylamido)-2-(3-methyl-η⁵-cyclopentadienyl)
  ethanediyltitanium bis(diethylamide)
1-(cyclohexylamido)-2-(3-methyl-η⁵-cyclopentadienyl)
  ethanediyltitanium dichloride
1-(cyclohexylamido)-2-(3-methyl-η⁵-cyclopentadienyl)
  ethanediyltitanium dibromide
1-(cyclohexylamido)-2-(3-methyl-η⁵-cyclopentadienyl)
  ethanediyltitanium bis(dimethylamide)
1-(cyclohexylamido)-2-(3-methyl-η⁵-cyclopentadienyl)
  ethanediyltitanium bis(diethylamide)
1-(methylamido)(3-ethyl-η⁵-cyclopentadienyl)
  ethanediylzirconium dichloride
1-(methylamido)(3-ethyl-η⁵-cyclopentadienyl)
  ethanediylzirconium bis(diethylamide)
1-(ethylamido)(3-ethyl-η⁵-cyclopentadienyl)
  ethanediylzirconium dichloride
1-(ethylamido)(3-ethyl-η⁵-cyclopentadienyl)
  ethanediylzirconium bis(diethylamide)
1-(isopropylamido)(3-ethyl-η⁵-cyclopentadienyl)
  ethanediylzirconium dichloride
1-(isopropylamido)(3-ethyl-η⁵-cyclopentadienyl)
  ethanediylzirconium bis(diethylamide)
1-(t-butylamido)(3-ethyl-η⁵-cyclopentadienyl)
  ethanediylzirconium dichloride
1-(t-butylamido)(3-ethyl-η⁵-cyclopentadienyl)
  ethanediylzirconium bis(diethylamide)
1-(phenylamido)(3-ethyl-η⁵-cyclopentadienyl)
  ethanediylzirconium dichloride
1-(phenylamido)(3-ethyl-η⁵-cyclopentadienyl)
  ethanediylzirconium bis(diethylamide)
1-(cyclohexylamido)-2-(3-methyl-η⁵-cyclopentadienyl)
  ethanediylzirconium dichloride
1-(cyclohexylamido)(3-ethyl-η⁵-cyclopentadienyl)
  ethanediylzirconium bis(diethylamide)
1-(methylamido)(3-ethyl-η⁵-cyclopentadienyl)
  ethanediyltitanium dichloride
1-(methylamido)(3-ethyl-η⁵-cyclopentadienyl)
  ethanediyltitanium dibromide
1-(methylamido)(3-ethyl-η⁵-cyclopentadienyl)
  ethanediyltitanium bis(dimethylamide)
1-(methylamido) (3-ethyl-η⁵-cyclopentadienyl)
  ethanediyltitanium bis(diethylamide)
1-(ethylamido)(3-ethyl-η⁵-cyclopentadienyl)
  ethanediyltitanium dichloride
1-(ethylamido)(3-ethyl-η⁵-cyclopentadienyl)
  ethanediyltitanium dibromide
1-(ethylamido)(3-ethyl-η⁵-cyclopentadienyl)
  ethanediyltitanium bis(dimethylamide)
1-(ethylamido)(3-ethyl-η⁵-cyclopentadienyl)
  ethanediyltitanium bis(diethylamide)
1-(isopropylamido)(3-ethyl-η⁵-cyclopentadienyl)
  ethanediyltitanium dichloride
1-(isopropylamido)(3-ethyl-η⁵-cyclopentadienyl)
  ethanediyltitanium dibromide
1-(isopropylamido)(3-ethyl-η⁵-cyclopentadienyl)
  ethanediyltitanium bis(dimethylamide)
1-(isopropylamido)(3-ethyl-η⁵-cyclopentadienyl)
  ethanediyltitanium bis(diethylamide)
1-(t-butylamido)(3-ethyl-η⁵-cyclopentadienyl)
  ethanediyltitanium dichloride
1-(t-butylamido)(3-ethyl-η⁵-cyclopentadienyl)
  ethanediyltitanium dibromide
1-(t-butylamido)(3-ethyl-η⁵-cyclopentadienyl)
  ethanediyltitanium bis(dimethylamide)
1-(t-butylamido)(3-ethyl-η⁵-cyclopentadienyl)
  ethanediyltitanium bis(diethylamide)

1-(phenylamido)(3-ethyl-$\eta^5$-cyclopentadienyl)ethanediyltitanium dichloride
1-(phenylamido)(3-ethyl-$\eta^5$-cyclopentadienyl)ethanediyltitanium dibromide
1-(phenylamido)(3-ethyl-$\eta^5$-cyclopentadienyl)ethanediyltitanium bis(dimethylamide)
1-(phenylamido)(3-ethyl-$\eta^5$-cyclopentadienyl)ethanediyltitanium bis(diethylamide)
1-(cyclohexylamido)-2-(3-methyl-$\eta^5$-cyclopentadienyl)ethanediyltitanium dichloride
1-(cyclohexylamido)(3-ethyl-$\eta^5$-cyclopentadienyl)ethanediyltitanium dibromide
1-(cyclohexylamido)(3-ethyl-$\eta^5$-cyclopentadienyl)ethanediyltitanium bis(dimethylamide)
1-(cyclohexylamido)(3-ethyl-$\eta^5$-cyclopentadienyl)ethanediyltitanium bis(diethylamide)
1-(methylamido)-2-(tetramethyl-$\eta^5$-cyclopentadienyl)ethanediylzirconium dichloride
1-(methylamido)-2-(tetramethyl-$\eta^5$-cyclopentadienyl)ethanediylzirconium bis(diethylamide)
1-(ethylamido)-2-(tetramethyl-$\eta^5$-cyclopentadienyl)ethanediylzirconium dichloride
1-(ethylamido)-2-(tetramethyl-$\eta^5$-cyclopentadienyl)ethanediylzirconium bis(diethylamide)
1-(isopropylamido)-2-(tetramethyl-$\eta^5$-cyclopentadienyl)ethanediylzirconium dichloride
1-(isopropylamido)-2-(tetramethyl-$\eta^5$-cyclopentadienyl)ethanediylzirconium bis(diethylamide)
1-(t-butylamido)-2-(tetramethyl-$\eta^5$-cyclopentadienyl)ethanediylzirconium dichloride
1-(t-butylamido)-2-(tetramethyl-$\eta^5$-cyclopentadienyl)ethanediylzirconium bis(diethylamide)
1-(phenylamido)-2-(tetramethyl-$\eta^5$-cyclopentadienyl)ethanediylzirconium dichloride
1-(phenylamido)-2-(tetramethyl-$\eta^5$-cyclopentadienyl)ethanediylzirconium bis(diethylamide)
1-(cyclohexylamido)-2-(tetramethyl-$\eta^5$-cyclopentadienyl)ethanediylzirconium dichloride
1-(cyclohexylamido)-2-(tetramethyl-$\eta^5$-cyclopentadienyl)ethanediylzirconium bis(diethylamide)
1-(methylamido)-2-(tetramethyl-$\eta^5$-cyclopentadienyl)ethanediyltitanium dichloride
1-(methylamido)-2-(tetramethyl-$\eta^5$-cyclopentadienyl)ethanediyltitanium dibromide
1-(methylamido)-2-(tetramethyl-$\eta^5$-cyclopentadienyl)ethanediyltitanium bis(dimethylamide)
1-(methylamido)-2-(tetramethyl-$\eta^5$-cyclopentadienyl)ethanediyltitanium bis(diethylamide)
1-(ethylamido)-2-(tetramethyl-$\eta^5$-cyclopentadienyl)ethanediyltitanium dichloride
1-(ethylamido)-2-(tetramethyl-$\eta^5$-cyclopentadienyl)ethanediyltitanium dibromide
1-(ethylamido)-2-(tetramethyl-$\eta^5$-cyclopentadienyl)ethanediyltitanium bis(dimethylamide)
1-(ethylamido)-2-(tetramethyl-$\eta^5$-cyclopentadienyl)ethanediyltitanium bis(diethylamide)
1-(isopropylamido)-2-(tetramethyl-$\eta^5$-cyclopentadienyl)ethanediyltitanium dichloride
1-(isopropylamido)-2-(tetramethyl-$\eta^5$-cyclopentadienyl)ethanediyltitanium dibromide
1-(isopropylamido)-2-(tetramethyl-$\eta^5$-cyclopentadienyl)ethanediyltitanium bis(dimethylamide)
1-(isopropylamido)-2-(tetramethyl-$\eta^5$-cyclopentadienyl)ethanediyltitanium bis(diethylamide)
1-(t-butylamido)-2-(tetramethyl-$\eta^5$-cyclopentadienyl)ethanediyltitanium dichloride
1-(t-butylamido)-2-(tetramethyl-$\eta^5$-cyclopentadienyl)ethanediyltitanium dibromide
1-(t-butylamido)-2-(tetramethyl-$\eta^5$-cyclopentadienyl)ethanediyltitanium bis(dimethylamide)
1-(t-butylamido)-2-(tetramethyl-$\eta^5$-cyclopentadienyl)ethanediyltitanium bis(diethylamide)
1-(phenylamido)-2-(tetramethyl-$\eta^5$-cyclopentadienyl)ethanediyltitanium dichloride
1-(phenylamido)-2-(tetramethyl-$\eta^5$-cyclopentadienyl)ethanediyltitanium dibromide
1-(phenylamido)-2-(tetramethyl-$\eta^5$-cyclopentadienyl)ethanediyltitanium bis(dimethylamide)
1-(phenylamido)-2-(tetramethyl-$\eta^5$-cyclopentadienyl)ethanediyltitanium bis(diethylamide)
1-(cyclohexylamido)-2-(tetramethyl-$\eta^5$-cyclopentadienyl)ethanediyltitanium dichloride
1-(cyclohexylamido)-2-(tetramethyl-$\eta^5$-cyclopentadienyl)ethanediyltitanium dibromide
1-(cyclohexylamido)-2-(tetramethyl-$\eta^5$-cyclopentadienyl)ethanediyltitanium bis(dimethylamide)
1-(cyclohexylamido)-2-(tetramethyl-$\eta^5$-cyclopentadienyl)ethanediyltitanium bis(diethylamide)
1-(methylamido)-2-(1-$\eta^5$-indenyl)ethanediylzirconium dichloride
1-(methylamido)-2-(1-$\eta^5$-indenyl)ethanediylzirconium bis(diethylamide)
1-(ethylamido)-2-(1-$\eta^5$-indenyl)ethanediylzirconium dichloride
1-(ethylamido)-2-(1-$\eta^5$-indenyl)ethanediylzirconium bis(diethylamide)
1-(isopropylamido)-2-(1-$\eta^5$-indenyl)ethanediylzirconium dichloride
1-(isopropylamido)-2-(1-$\eta^5$-indenyl)ethanediylzirconium bis(diethylamide)
1-(t-butylamido)-2-(1-$\eta^5$-indenyl)ethanediylzirconium dichloride
1-(t-butylamido)-2-(1-$\eta^5$-indenyl)ethanediylzirconium bis(diethylamide)
1-(phenylamido)-2-(1-$\eta^5$-indenyl)ethanediylzirconium dichloride
1-(phenylamido)-2-(1-$\eta^5$-indenyl)ethanediylzirconium bis(diethylamide)
1-(cyclohexylamido)-2-(1-$\eta^5$-indenyl)ethanediylzirconium dichloride
1-(cyclohexylamido)-2-(1-$\eta^5$-indenyl)ethanediylzirconium bis(diethylamide)
1-(methylamido)-2-(1-$\eta^5$-indenyl)ethanediyltitanium dichloride
1-(methylamido)-2-(1-$\eta^5$-indenyl)ethanediyltitanium dibromide
1-(methylamido)-2-(1-$\eta^5$-indenyl)ethanediyltitanium bis(dimethylamide)
1-(methylamido)-2-(1-$\eta^5$-indenyl)ethanediyltitanium bis(diethylamide)
1-(ethylamido)-2-(1-$\eta^5$-indenyl)ethanediyltitanium dichloride
1-(ethylamido)-2-(1-$\eta^5$-indenyl)ethanediyltitanium dibromide 1-(ethylamido)-2-(1-η⁵-indenyl)ethanediyltitanium bis(dimethylamide)

1-(ethylamido)-2-(1-η⁵-indenyl)ethanediyltitanium bis(diethylamide)

1-(isopropylamido)-2-(1-η⁵-indenyl)ethanediyltitanium dichloride 1-(isopropylamido)-2-(1-η⁵-indenyl)ethanediyltitanium dibromide 1-(isopropylamido)-2-(1-η⁵-indenyl)ethanediyltitanium bis(dimethylamide)

1-(isopropylamido)-2-(1-η⁵-indenyl)ethanediyltitanium bis(diethylamide)

1-(t-butylamido)-2-(1-η⁵-indenyl)ethanediyltitanium dichloride 1-(t-butylamido)-2-(1-η⁵-indenyl)ethanediyltitanium dibromide 1-(t-butylamido)-2-(1-η⁵-indenyl)ethanediyltitanium bis(dimethylamide)

1-(t-butylamido)-2-(1-η⁵-indenyl)ethanediyltitanium bis(diethylamide)

1-(phenylamido)-2-(1-η⁵-indenyl)ethanediyltitanium dichloride 1-(phenylamido)-2-(1-η⁵-indenyl)ethanediyltitanium dibromide 1-(phenylamido)-2-(1-η⁵-indenyl)ethanediyltitanium bis(dimethylamide)

1-(phenylamido)-2-(1-η⁵-indenyl)ethanediyltitanium bis(diethylamide)

1-(phenylamido)-2-(1-η⁵-indenyl)ethanediyltitanium dichloride 1-(cyclohexylamido)-2-(1-η⁵-indenyl)ethanediyltitanium dibromide 1-(cyclohexylamido)-2-(1-η⁵-indenyl)ethanediyltitanium bis(diethylamide)

1-(cyclohexylamido)-2-(1-η⁵-indenyl)ethanediyltitanium bis(dimethylamide)

1-(methylamido)-2-(9-η⁵-fluorenyl)ethanediylzirconium dichloride 1-(methylamido)-2-(9-η⁵-fluorenyl)ethanediylzirconium bis(diethylamide)

1-(ethylamido)-2(9-η⁵-fluorenyl)ethanediylzirconium dichloride 1-(ethylamido)-2-(9-η⁵-fluorenyl)ethanediylzirconium bis(diethylamide)

1-(isopropylamido)-2-(9-η⁵-fluorenyl)ethanediylzirconium dichloride 1-(isopropylamido)-2-(9-η⁵-fluorenyl)ethanediylzirconium bis(diethylamide)

1-(t-butylamido)-2-(9-η⁵-fluorenyl)ethanediylzirconium dichloride 1-(t-butylamido)-2-(9-η⁵-fluorenyl)ethanediylzirconium bis(diethylamide)

1-(phenylamido)-2-(9-η⁵-fluorenyl)ethanediylzirconium dichloride 1-(phenylamido)-2-(9-η⁵-fluorenyl)ethanediylzirconium bis(diethylamide)

1-(cyclohexylamido)-2-(9-η⁵-fluorenyl)ethanediylzirconium dichloride 1-(cyclohexylamido)-2-(9-η⁵-fluorenyl)ethanediylzirconium bis(diethylamide)

1-(methylamido)-2-(9-η⁵-fluorenyl)ethanediyltitanium dichloride 1-(methylamido)-2-(9-η⁵-fluorenyl)ethanediyltitanium dibromide 1-(methylamido)-2-(9-η⁵-fluorenyl)ethanediyltitanium bis(dimethylamide)

1-(methylamido)-2-(9-η⁵-fluorenyl)ethanediyltitanium bis(diethylamide)

1-(ethylamido)-2-(9-η⁵-fluorenyl)ethanediyltitanium dichloride 1-(ethylamido)-2-(9-η⁵-fluorenyl)ethanediyltitanium dibromide 1-(ethylamido)-2-(9-η⁵-fluorenyl)ethanediyltitanium bis(dimethylamide)

1-(ethylamido)-2-(9-η⁵-fluorenyl)ethanediyltitanium bis(diethylamide)

1-(isopropylamido)-2-(9-η⁵-fluorenyl)ethanediyltitanium dichloride 1-(isopropylamido)-2-(9-η⁵-fluorenyl)ethanediyltitanium dibromide 1-(isopropylamido)-2-(9-η⁵-fluorenyl)ethanediyltitanium bis(dimethylamide)

1-(isopropylamido)-2-(9-η⁵-fluorenyl)ethanediyltitanium bis(diethylamide)

1-(t-butylamido)-2-(9-η⁵-fluorenyl)ethanediyltitanium dichloride 1-(t-butylamido)-2-(9-η⁵-fluorenyl)ethanediyltitanium dibromide 1-(t-butylamido)-2-(9-η⁵-fluorenyl)ethanediyltitanium bis(dimethylamide)

1-(t-butylamido)-2-(9-η⁵-fluorenyl)ethanediyltitanium bis(diethylamide)

1-(phenylamido)-2-(9-η⁵-fluorenyl)ethanediyltitanium dichloride 1-(phenylamido)-2-(9-η⁵-fluorenyl)ethanediyltitanium dibromide 1-(phenylamido)-2-(9-η⁵-fluorenyl)ethanediyltitanium bis(dimethylamide)

1-(phenylamido)-2-(9-η⁵-fluorenyl)ethanediyltitanium bis(diethylamide)

1-(cyclohexylamido)-2-(9-η⁵-fluorenyl)ethanediyltitanium dichloride 1-(cyclohexylamido)-2-(9-η⁵-fluorenyl)ethanediyltitanium dibromide 1-(cyclohexylamido)-2-(9-η⁵-fluorenyl)ethanediyltitanium bis(dimethylamide)

1-(cyclohexylamido)-2-(9-η⁵-fluorenyl)ethanediyltitanium bis(diethylamide)

The metal complex to be used in the process of the invention can also be present in dimeric form. Examples of such complexes are:

bis[(isopropylamido)(η⁵-cyclopentadienyl)dimethylsilane]zirconium bis[(t-butylamido)(η⁵-cyclopentadienyl)dimethylsilane]zirconium bis[(phenylamido)(η⁵-cyclopentadienyl)dimethylsilane]zirconium bis[(cyclohexylamido)(η⁵-cyclopentadienyl)dimethylsilane]zirconium bis[(isopropylamido)(3-methyl-η⁵-cyclopentadienyl)dimethylsilane]zirconium bis[(t-butylamido)(3-methyl-η⁵-cyclopentadienyl)dimethylsilane]zirconium bis[(phenylamido)(3-methyl-η⁵-cyclopentadienyl)dimethylsilane]zirconium bis[(cyclohexylamido)(3-methyl-$\eta^5$-cyclopentadienyl)dimethylsilane]zirconium
bis[(isopropylamido)(tetramethyl-$\eta^5$-cyclopentadienyl)dimethylsilane]zirconium
bis[(t-butylamido)(tetramethyl-$\eta^5$-cyclopentadienyl)dimethylsilane]zirconium
bis[(phenylamido)(tetramethyl-$\eta^5$-cyclopentadienyl)dimethylsilane]zirconium
bis[(cyclohexylamido)(tetramethyl-$\eta^5$-cyclopentenyl)dimethylsilane]zirconium
bis[(isopropylamido)(9-$\eta^5$-indenyl)dimethylsilane]zirconium
bis[(t-butylamido)(1-$\eta^5$-indenyl)dimethylsilane]zirconium
bis[(phenylamido)(1-$\eta^5$-indenyl)dimethylsilane]zirconium
bis[(cyclohexylamido)(1-$\eta^5$-indenyl)dimethylsilane]zirconium
bis[(isopropylamido)(9-$\eta^5$-fluorenyl)dimethylsilane]zirconium
bis[(t-butylamido)(9-$\eta^5$-fluorenyl)dimethylsilane]zirconium
bis[(phenylamido)(9-$\eta^5$-fluorenyl)dimethylsilane]zirconium
bis[(cyclohexylamido)(9-$\eta^5$-fluorenyl)dimethylsilane]zirconium
bis[(isopropylamido)($\eta^5$-cyclopentadienyl)dimethylsilane]titanium
bis[(t-butylamido)($\eta^5$-cyclopentadienyl)dimethylsilane]titanium
bis[(phenylamido)($\eta^5$-cyclopentadienyl)dimethylsilane]titanium
bis[(cyclohexylamido)($\eta^5$-cyclopentadienyl)dimethylsilane]titanium
bis[(isopropylamido)(3-methyl-$\eta^5$-cyclopentadienyl)dimethylsilane]titanium
bis[(t-butylamido)(3-methyl-$\eta^5$-cyclopentadienyl)dimethylsilane]titanium
bis[(phenylamido)(3-methyl-$\eta^5$-cyclopentadienyl)dimethylsilane]titanium
bis[(cyclohexylamido)(3-methyl-$\eta^5$-cyclopentadienyl)dimethylsilane]titanium
bis[(isopropylamido)(tetramethyl-$\eta^5$-cyclopentadienyl)dimethylsilane]titanium
bis[(t-butylamido)(tetramethyl-$\eta^5$-cyclopentadienyl)dimethylsilane]titanium
bis[(phenylamido)(tetramethyl-$\eta^5$-cyclopentadienyl)dimethylsilane]titanium
bis[(cyclohexylamido)(tetramethyl-$\eta^5$-cyclopentadienyl)dimethylsilane]titanium
bis[(isopropylamido)(1-$\eta^5$-indenyl)dimethylsilane]titanium
bis[(t-butylamido)(1-$\eta^5$-indenyl)dimethylsilane]titanium
bis[(phenylamido)(1-$\eta^5$-indenyl)dimethylsilane]titanium
bis[(cyclohexylamido)(1-$\eta^5$-indenyl)dimethylsilane]titanium
bis[(isopropylamido)(9-$\eta^5$-fluorenyl)dimethylsilane]titanium
bis[(t-butylamido)(9-$\eta^5$-fluorenyl)dimethylsilane]titanium
bis[(phenylamido)(9-$\eta^5$-fluorenyl)dimethylsilane]titanium
bis[(cyclohexylamido)(9-$\eta^5$-fluorenyl)dimethylsilane]titanium
bis[(isopropylamido)($\eta^5$-cyclopentadienyl)dimethylsilane]hafnium
bis[(t-butylamido)($\eta^5$-cyclopentadienyl)dimethylsilane]hafnium
bis[(phenylamido)($\eta^5$-cyclopentadienyl)dimethylsilane]hafnium
bis[(cyclohexylamido)($\eta^5$-cyclopentadienyl)dimethylsilane]hafnium
bis[(isopropylamido)(3-methyl-$\eta^5$-cyclopentadienyl)dimethylsilane]hafnium
bis[(t-butylamido)(3-methyl-cyclopentadienyl)dimethylsilane]hafnium
bis[(phenylamido)(3-methyl-cyclopentadienyl)dimethylsilane]hafnium
bis[(cyclohexylamido)(3-methyl-$\eta^5$-cyclopentadienyl)dimethylsilane]hafnium
bis[(isopropylamido)(tetramethyl-$\eta^5$-cyclopentadienyl)dimethylsilane]hafnium
bis[(t-butylamido)(tetramethyl-$\eta^5$-cyclopentadienyl)dimethylsilane]hafnium
bis[(phenylamido)(tetramethyl-$\eta^5$-cyclopentadienyl)dimethylsilane]hafnium
bis[(cyclohexylamido)(tetramethyl-$\eta^5$-cyclopentadienyl)dimethylsilane]hafnium
bis[(isopropylamido)(1-$\eta^5$-indenyl)dimethylsilane]hafnium
bis[(t-butylamido)(1-$\eta^5$-indenyl)dimethylsilane]hafnium
bis[(phenylamido)(1-$\eta^5$-indenyl)dimethylsilane]hafnium
bis[(cyclohexylamido)(1-$\eta^5$-indenyl)dimethylsilane]hafnium
bis[(isopropylamido)(9-$\eta^5$-fluorenyl)dimethylsilane]hafnium
bis[(t-butylamido)(9-$\eta^5$-fluorenyl)dimethylsilane]hafnium
bis[(phenylamido)(9-$\eta^5$-fluorenyl)dimethylsilane]hafnium
bis[(cyclohexylamido)(9-$\eta^5$-fluorenyl)dimethylsilane]hafnium.

The preparation of the metal complexes to be used in the process of the invention is described in detail in EP-A-426 815.

In the process of the invention, the cocatalyst used is preferably an aluminoxane which preferably has the formula IIa for the linear type and/or the formula IIb for the cyclic type,

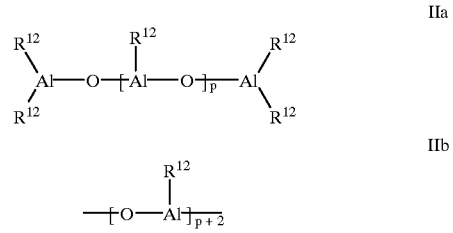

where, in the formulae IIa and IIb, the radicals R are identical or different and are each a $C_1$–$C_6$-alkyl group, a $C_6$–$C_{18}$-aryl group, benzyl or hydrogen and n is an integer from 2 to 50, preferably from 10 to 35. Preferably, the radicals $R^{12}$ are identical and are methyl, isobutyl, phenyl or benzyl, particularly preferably methyl.

If the radicals $R^{12}$ are different, they are preferably methyl and hydrogen or alternatively methyl and isobutyl, with hydrogen or isobutyl preferably being present in a proportion by number of from 0.01 to 40% (of the radicals $R^{12}$).

The aluminoxane can be prepared in various ways by known methods. One of the methods is, for example, reacting an aluminum hydrocarbon compound and/or a hydridoaluminum hydrocarbon compound with water (gaseous, solid, liquid or bound, for example as water of crystallization) in an inert solvent (such as toluene). To prepare an aluminoxane having different alkyl groups $R^{12}$, two different trialkylaluminums ($AlR_3+AlR'_3$) corresponding to the desired composition are reacted with water (S. Pasynkiewicz, Polyhedron 9 (1990) 429, EP-A-302 424). The precise three-dimensional structure of the aluminoxanes is not known.

Regardless of the method of preparation, all aluminoxane solutions have in common a varying content of unreacted aluminum starting compound which is present in free form or as adduct.

It is also possible to apply the aluminoxane to a support and then to use it as a suspension in supported form. A number of methods of applying the aluminoxane to a support are known (EP-A-578 838). Silica gel can function as support.

It is possible to preactivate the metal complex to be used in the process of the invention by means of a cocatalyst, in particular an aluminoxane, prior to use in the polymerization reaction. This significantly increases the polymerization activity.

The preactivation of the transition metal compound is carried out in solution. Here, the metal complex is preferably dissolved in a solution of the aluminoxane in an inert hydrocarbon. Suitable inert hydrocarbons are aliphatic or aromatic hydrocarbons. Preference is given to using toluene.

The concentration of the aluminoxane in the solution is in the range from about 1% by weight to the saturation limit, preferably from 5 to 30% by weight, in each case based on the total solution. The metal complex can be used in the same concentration, but it is preferably used in an amount of from $10^{-4}$ to 1 mol per mol of aluminoxane. The preactivation time is from 5 minutes to 60 hours, preferably from 5 to 60 minutes. The preactivation is carried out at a temperature of from −78 to 100° C., preferably from 0 to 70° C.

A prepolymerization can be carried out with the aid of the metal complex. For the prepolymerization, preference is given to using the (or one of the) olefin(s) used in the polymerization.

The metal complex can also be applied to a support. Suitable supports are, for example, silica gels, aluminum oxides, solid aluminoxane or other inorganic support materials. A polyolefin powder in finely divided form is also a suitable support material.

A further possible embodiment of the process of the invention comprises using a salt-like compound of the formula $R_xNH_{4-x}BR'_4$ or of the formula $R_3PHBR'_4$ as cocatalyst in place of or in addition to an aluminoxane. Here, x=1, 2 or 3, R=alkyl or aryl, identical or different, and R'=aryl which may be fluorinated or partially fluorinated. In this case, the catalyst comprises the reaction product of a metal complex with one of the compounds mentioned (EP-A-277 004).

If solvents are added to the reaction mixture, they are customary inert solvents such as aliphatic or cycloaliphatic hydrocarbons, petroleum fractions or hydrogenated diesel oil fractions or toluene.

The metal complex is preferably employed in a concentration, based on the transition metal, of from $10^{-1}$ to $10^{-8}$ mol, preferably from $10^{-2}$ to $10^{-7}$ mol, particularly preferably from $10^{-3}$ to $10^{-7}$ mol, of transition metal per dm$^3$ of reactor volume. The aluminoxane is used in a concentration of from $10^{-4}$ to $10^{-1}$ mol, preferably from $10^{-4}$ to $2\times10^{-2}$ mol, per dm$^3$ of reactor volume, based on the aluminum content. However, higher concentrations are also possible in principle.

The invention provides a process for preparing a cycloolefin copolymer by polymerization of from 0.1 to 99.9% by weight, based on the total amount of monomers, of at least one polycyclic olefin of the formula III, IV, IV', V, VI, VII or VIII.

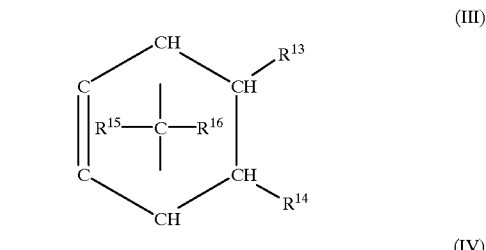

(III)

(IV)

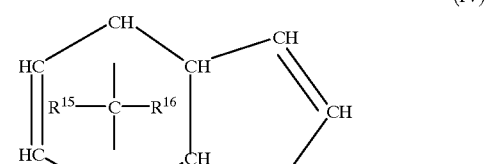

(IV')

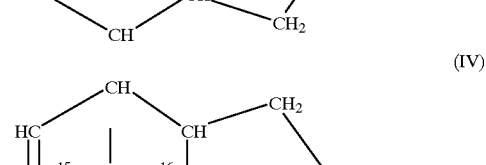

(V)

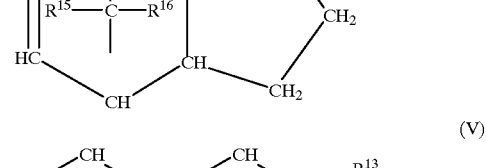

(VI)

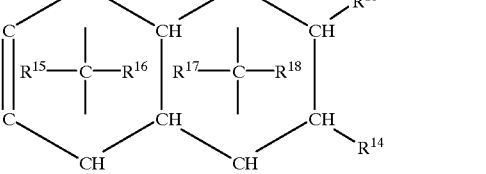

-continued (VII)

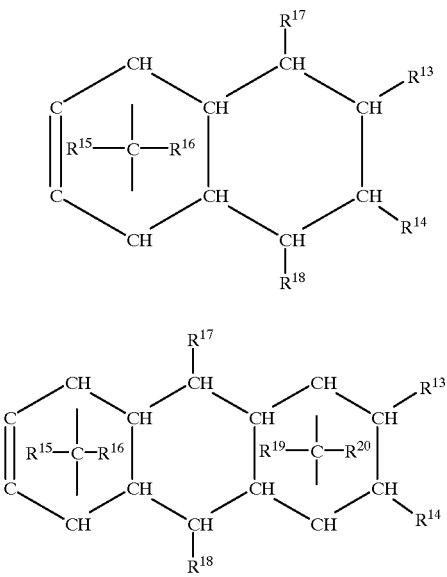

(VIII)

where $R^{13}, R^{14}, R^{15}, R^{16}, R^{17}, R^{18}, R^{19}$ and $R^{20}$ are identical or different and are each a hydrogen atom or a hydrocarbon radical, where identically numbered radicals in the various formulae can also have different meanings, from 0 to 99.9% by weight, based on the total amount of the monomers, of at least one monocyclic olefin of the formula IX (IX)

where q is from 2 to 10, and from 0.1 to 99.9% by weight, based on the total amount of monomers, of at least one acyclic 1-olefin of the formula X (X)

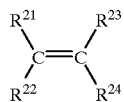

where $R^{21}, R^{22}, R^{23}$ and $R^{24}$ are identical or different and are each a hydrogen atom or a hydrocarbon radical, preferably a $C_6$–$C_{10}$-aryl radical or a $C_1$–$C_8$-alkyl radical, at temperatures of from −78 to 150° C., in particular from 0 to 100° C., and a pressure of from 0.01 to 64 bar.

Preference is given to cycloolefins of the formula III or V in which $R^{13}$, $R^{14}$, $R^{15}$, $R^{16}$, $R^{17}$, $R^{18}$, $R^{19}$ and $R^{20}$ are identical or different and are each a hydrogen atom or a hydrocarbon radical, in particular a $C_6$–$C_{10}$-aryl radical or a $C_1$–$C_8$-alkyl radical, where identically numbered radicals in the various formulae can have different meanings.

If desired, one or more monocyclic olefins of the formula IX are used for the polymerization.

Preference is also given to an acyclic olefin of the formula X in which $R^{21}$, $R^{22}$, $R^{23}$ and $R^{24}$ are identical or different and are each a hydrogen atom or a hydrocarbon radical, preferably a $C_6$–$C_{10}$-aryl radical or a $C_1$–$C_8$-alkyl radical, for example ethylene or propylene.

In particular, copolymers of polycyclic olefins, preferably of the formulae III and V, with ethylene are prepared.

Particularly preferred polycyclic olefins are norbornene and tetracyclododecene; these may be substituted by $C_1$–$C_6$-alkyl. They are preferably copolymerized with ethylene. Very particular preference is given to ethylene-norbornene copolymers and ethylene-tetracyclododecene copolymers.

The polycyclic olefin is used in an amount of from 0.1 to 99.9% by weight and the monocyclic olefin is used in an amount of from 0 to 99.9% by weight, in each case based on the total amount of monomers.

The concentration of the acyclic olefin used is determined by its solubility in the reaction medium at the given pressure and the given temperature.

For the purposes of the present invention, polycyclic olefins, monocyclic olefins and acyclic olefins include mixtures of two or more olefins of the respective type. This means that it is possible to prepare not only polycyclic bicopolymers but also tercopolymers and multicopolymers by the process of the invention. Copolymers of monocyclic olefins and acyclic olefins can also be obtained by the process described.

Among the monocyclic olefins, preference is given to cyclopentene, which may be substituted.

Owing to their low susceptibility to oxidation and crosslinking, preference is given to cycloolefin copolymers which consist of units derived from monomers which have, apart from the olefinic double bond required for the polymerization, no further unsaturated functionalities.

The process of the invention is preferably carried out at temperatures of from −78 to 150° C., in particular from 0 to 100° C., and a pressure of from 0.01 to 64 bar.

The process of the invention relates to the preparation of cycloolefin copolymers which comprise at least 5 mol % of the cyclic olefin.

In the preparation of copolymers, the molar ratio of the polycyclic olefin to the open-chain olefin used can be varied within a wide range. Preference is given to using molar ratios of cycloolefin to open-chain olefin of from 3:1 to 200:1. Selection of the polymerization temperature, the concentration of the catalyst components and the molar ratio or pressure of the gaseous, open-chain olefin enables the proportion of comonomer incorporated to be controlled almost as desired. Preference is given to incorporated proportions of the cyclic components of from 5 to 80 mol %, particularly preferably from 10 to 60 mol % and very particularly preferably from 15 to 40 mol %.

The cycloolefin copolymers prepared by the process of the invention have glass transition temperatures of from −50 to 220° C. Preference is given to glass transition temperatures of from −30 to 180° C., particularly preferably from −20 to 150° C., very particularly preferably from 0 to 100° C.

The polymerization can also be carried out in a plurality of stages, so that block copolymers can also be formed (DE-A-42 05 416).

The mean molar mass of the polymer formed can be controlled in a known manner by metering-in hydrogen, varying the catalyst concentration or varying the temperature.

The cycloolefin copolymers prepared by the process of the invention have mass average molar masses $M_w$ of from 1000 to 10,000,000 g/mol. Preference is given to mass average molar masses of from 10,000 to 5,000,000 g/mol, particularly preferably from 50,000 to 2,000,000 g/mol.

The cycloolefin copolymers prepared by the process of the invention have viscosity numbers of from 10 to 1000 ml/g, preference is given to viscosity numbers of from 30 to 500 ml/g, particularly preferably from 50 to 300 ml/g.

In cycloolefin copolymers which have not been prepared by the process of the invention, the low molar mass of the cycloolefin copolymer leads to poor material properties such as low toughness, so that these materials are of little interest for commercial use.

It has now surprisingly been found that cycloolefin copolymers having significantly higher molar masses can be prepared over a wide range of glass transition temperatures by the process of the invention. The cycloolefin copolymers prepared by the process of the invention have a higher melting resistance and toughness and are therefore of particular interest for commercial use.

The polydispersity $M_w/M_n$ of the copolymers has values of from 1.6 to 3.5 and is therefore quite narrow. This results in a property profile which makes the copolymers particularly suitable for injection molding. It is also possible to obtain a polydispersity beyond the indicated limits by selection of the catalyst system. Apart from monomodal distributions, cycloolefin copolymers having bimodal or multimodal distributions can also be prepared by the process of the invention.

If catalyst systems which are not as specified in the process of the invention are chosen, it is possible for ethylene polymers which reduce the transparency of the material to be formed in addition ot the cycloolefin copolymers. In addition, the insolubility of these ethylene polymers leads to formation of deposits during the process, which deposits interfere with the production process and require regular cleaning work.

It has now surprisingly been found that no ethylene polymers are formed when employing the catalyst system to be used in the process of the invention. The process of the invention enables cycloolefin copolymers of high transparency to be prepared.

The process of the invention gives a high yield of polymer based on the amount of catalyst used. The process of the invention thus represents a very economical process compared to the prior art, since the catalyst costs are lower because of the high activity of the catalyst.

Both in extrusion and in injection molding, neither decomposition reactions nor a decrease in viscosity have been found at temperatures of 30° C.

The materials prepared according to the invention are particularly suitable for producing moldings such as extruded parts (films, sheets, hoses, pipes, rods and fibers) or injection-molded articles of any shape and size. Important properties of the materials of the invention are their transparency, their purity, the favorable mechanical properties, the low water absorption and the high barrier action against water vapor.

The index of refraction of the reaction products described in the following examples determined using an Abbe refractometer and mixed light is in the range from 1.520 to 1.555. Since the index of refraction is very close to that of crown glass (n=1.51), the products according to the invention can be employed as a substitute for glass in various applications in the optical field, for example lenses, prisms, support plates and films for optical data storage, for video disks, for compact disks, as covering and focusing plates for solar cells, as covering and scattering plates for power optics, as optical waveguides in the form of fibers or films. Owing to the property profile described, the materials prepared according to the invention are of great interest in the field of medical technology. They are used as materials for catheters, bags for infusion solutions or dialysis fluid, for tubing, containers, implants and components of medical apparatus. In addition, they are used in the form of injection-molded parts for containers, bottles, vials and syringes for the storage, exchange or application of liquids. The properties of the cycloolefin copolymers prepared according to the invention make them particularly suitable for use in the form of films for the pharmaceutical, food and industrial sectors.

In impact-modified form, the materials prepared according to the invention can also be used as structural materials in various engineering areas (DE-A-42 13 219).

The polymers obtained according to the invention can also be used for producing polymer blends. The blends can be produced in the melt or in solution. The blends have a property combination of the components which is in each case favorable for particular applications. For blends with the polymers of the invention, preference is given to using the following polymers:

polyethylene, polypropylene, 1-(ethylene-propylene) copolymers, polybutylene, poly-(4-methyl-1-pentene), polyisoprene, polyisobutylene, natural rubber, poly-1-(methyl methacrylate), further polymethacrylates, polyacrylates, (acrylate-methacrylate)copolymers, polystyrene, (styrene-acrylonitrile)copolymers, bisphenol A polycarbonate, further polycarbonates, aromatic polyester carbonates, polyethylene terephthalate, polybutylene terephthalate, amorphous polyarylates, nylon 6, nylon 66, further polyamides, polyaramides, polyether ketones, polyoxymethylene, polyoxyethylene, polyurethanes, polysulfones, polyether sulfones, polyvinylidene fluoride.

Surfaces of workpieces and moldings produced from the cycloolefin copolymers of the invention can be modified by suitable methods such as fluorination, corona treatment, flame treatment and plasma treatment. In this way, properties such as adhesion or printability can be altered without the requirement of the present invention being impaired.

The process of the invention gives transparent cycloolefin copolymers having high molar masses.

The glass transition temperatures $T_g$ reported in the following examples were determined by means of DSC (differential scanning colorimetry) at a heating rate of 20° C./min. The viscosity numbers VN reported were determined in decalin at 135° C. in accordance with DIN 53728. The mass average molar mass and the polydispersity were determined by means of GPC.

The invention is illustrated by the following examples:

EXAMPLES

Example 1

600 cm of an 85% strength by weight solution of norbornene in toluene are placed in a 1.5 dm$^3$ autoclave which has previously been thoroughly purged with ethene. The solution was saturated with ethene by multiple pressurization with ethene (18 bar). 10 cm$^3$ of methylaluminoxane solution in toluene (10% strength by weight methylaluminoxane solution having a molar mass of 1300 g/mol according to cryoscopic determination) were metered in countercurrent into the reactor which had been prepared in this way and the mixture was stirred for 30 minutes at 70° C. A solution of 4.7 mg of (t-butylamido)(1-η$^5$-indenyl) dimethylsilanetitanium dichloride in 10 cm of methylaluminoxane solution in toluene was added after preactivation for 15 minutes.

While stirring (750 rpm), polymerization was carried out for one hour, with the ethene pressure being maintained at 18 bar by metering in further amounts.

After the end of the reaction time, the polymerization mixture was drained into a vessel and immediately introduced into 5 dm$^3$ of acetone, stirred for 10 minutes and the precipitated product was subsequently filtered off. The filter cake was washed alternately with three portions each of 10% hydrochloric acid and acetone, the residue was slurried in acetone and filtered off again. The polymer which had been purified in this way was dried at 80° C. under reduced pressure (0.2 bar) for 15 hours.

This gave 29 g of colorless polymer which had a glass transition temperature of 103° C., a viscosity number of 271 ml/g, a weight average molar mass of 270,000 g/mol and a polydispersity of 2.0.

Example 2

600 cm$^3$ of an 85% strength by weight solution of norbornene in toluene are placed in a 1.5 dm$^3$ autoclave which has previously been thoroughly purged with ethene. The solution was saturated with ethene by multiple pressurization with ethene (18 bar). 10 cm$^3$ of methylaluminoxane solution in toluene (10% strength by weight methylaluminoxane solution having a molar mass of 1300 g/mol according to cryoscopic determination) were metered in countercurrent into the reactor which had been prepared in this way and the mixture was stirred for 30 minutes at 70° C. A solution of 3.7 mg of (t-butylamido)dimethyl(3-methyl-$\eta^5$-cyclopentadienyl)silanetitanium dichloride in 10 cm$^3$ of methylaluminoxane solution in toluene was added after preactivation for 15 minutes.

While stirring (750 rpm), polymerization was carried out for one hour, with the ethene pressure being maintained at 18 bar by metering in further amounts.

After the end of the reaction time, the polymerization mixture was drained into a vessel and immediately introduced into 5 dm$^3$ of acetone, stirred for 10 minutes and the precipitated product was subsequently filtered off. The filter cake was washed alternately with three portions each of 10% hydrochloric acid and acetone, the residue was slurried in acetone and filtered off again. The polymer which had been purified in this way was dried at 80° C. under reduced pressure (0.2 bar) for 15 hours.

This gave 31 g of colorless polymer which had a glass transition temperature of 102° C., a viscosity number of 291 ml/g, a weight average molar mass of 253,000 g/mol and a polydispersity 2.1.

Example 3

600 cm of an 85% strength by weight solution of norbornene in toluene are placed in a 1.5 dm$^3$ autoclave which has previously been thoroughly purged with ethene. The solution was saturated with ethene by multiple pressurization with ethene (6 bar). 10 cm of methylaluminoxane solution in toluene (10% strength by weight methylaluminoxane solution having a molar mass of 1300 g/mol according to cryoscopic determination) were metered in countercurrent into the reactor which had been prepared in this way and the mixture was stirred for 30 minutes at 70° C. A solution of 7.8 mg of (t-butylamido)dimethyl(3-methyl-$\eta^5$-cyclopentadienyl)silanetitanium dichloride in 10 cm$^3$ of methylaluminoxane solution in toluene was added after preactivation for 15 minutes.

While stirring (750 rpm), polymerization was carried out for one hour, with the ethene pressure being maintained at 6 bar by metering in further amounts.

After the end of the reaction time, the polymerization mixture was drained into a vessel and immediately introduced into 5 dm$^3$ of acetone, stirred for 10 minutes and the precipitated product was subsequently filtered off. The filter cake was washed alternately with three portions each of 10% hydrochloric acid and acetone, the residue was slurried in acetone and filtered off again. The polymer which had been purified in this way was dried at 80° C. under reduced pressure (0.2 bar) for 15 hours.

This gave 10 g of colorless polymer which had a glass transition temperature of 122° C., a viscosity number of 180 ml/g, a weight average molar mass of 143,000 g/mol and a polydispersity 1.8.

Examples 4 and 5

600 cm of a solution of norbornene in toluene are placed in a 1.5 dm$^3$ autoclave which has previously been thoroughly purged with ethene. The solution was saturated with ethene by multiple pressurization with ethene (18 bar). 10 cm$^3$ of methylaluminoxane solution in toluene (10% strength by weight methylaluminoxane solution having a molar mass of 1300 g/mol according to cryoscopic determination) were metered in countercurrent into the reactor which had been prepared in this way and the mixture was stirred for 30 minutes at 70° C. A solution of (t-butylamido)(1-$\eta^5$-indenyl)dimethylsilanetitanium dichloride in 10 cm$^3$ of methylaluminoxane solution in toluene was added after preactivation for 15 minutes.

While stirring (750 rpm), polymerization was carried out for one hour, with the ethene pressure being maintained at 18 bar by metering in further amounts.

After the end of the reaction time, the polymerization mixture was drained into a vessel and immediately introduced into 5 dm$^3$ of acetone, stirred for 10 minutes and the precipitated product was subsequently filtered off. The filter cake was washed alternately with three portions each of 10% hydrochloric acid and acetone, the residue was slurried in acetone and filtered off again. The polymer which had been purified in this way was dried at 80° C. under reduced pressure (0.2 bar) for 15 hours.

This gave a colorless polymer. The further reaction conditions and the characteristic data of the polymer are summarized in Table 1.

TABLE 1

| Ex. | Monomer solution [% by weight of norbornene] | Amount of catalyst [mg] | Yield [g] | Tg [° C.] | VN [ml/g] | Mw [g/mol] | Mw/Mn |
| --- | --- | --- | --- | --- | --- | --- | --- |
| 4 | 50 | 3.8 | 53 | 80 | 343 | 199,000 | 1.8 |
| 5 | 30 | 3.9 | 71 | 57 | 272 | 171,000 | 1.9 |

Examples 6 and 7

600 cm$^3$ of a solution of norbornene in toluene are placed in a 1.5 dm$^3$ autoclave which has previously been thoroughly purged with ethane. The solution was saturated with ethene by multiple pressurization with ethene (18 bar). 10 cm of methylaluminoxane solution in toluene (10% strength by weight methylaluminoxane solution having a molar mass of 1300 g/mol according to cryoscopic determination) were metered in countercurrent into the reactor which had been prepared in this way and the mixture was stirred for 30 minutes at 70° C. A solution of (t-butylamido)dimethyl(3-methyl-$\eta^5$-cyclopentadienyl)silanetitanium dichloride in 10 cm$^3$ of methylaluminoxane solution in toluene was added after preactivation for 15 minutes.

Polymerization was carried out while stirring (750 rpm) for one hour, with the ethene pressure being maintained at 18 bar by metering in further amounts.

After the end of the reaction time, the polymerization mixture was drained into a vessel and immediately introduced into 5 dm$^3$ of acetone, stirred for 10 minutes and the precipitated product was subsequently filtered off. The filter cake was washed alternately with three portions each of 10% hydrochloric acid and acetone, the residue was slurried in acetone and filtered off again. The polymer which had been purified in this way was dried at 80° C. under reduced pressure (0.2 bar) for 15 hours.

This gave a colorless polymer. The further reaction conditions and the characteristic data of the polymer are summarized in Table 2.

which had previously been purged thoroughly with ethene. The solution was saturated with ethene by multiple pressurization with ethene (6.8 bar). 1 cm$^3$ of methylaluminoxane solution in toluene (10% strength by weight methylaluminoxane solution having a molar mass of 1300 g/mol according to cryoscopic determination) was metered in countercurrent into the reactor which had been prepared in this way and the mixture was stirred for 30 minutes at 70° C. A solution of 0.29 mg of (t-butylamido)dimethyl(tetramethyl-$\eta^5$-cyclopentadienyl)silanetitanium dichloride in 1 cm$^3$ of methylaluminoxane solution in toluene was added after preactivation for 15 minutes.

While stirring (800 rpm), polymerization was carried out for 1 hour, with the ethene pressure being maintained at 6.8 bar by metering in further amounts.

After the end of the reaction time, the polymerization mixture was drained into a vessel and immediately introduced into 5 dm$^3$ of acetone, stirred for 10 minutes and the precipitated product was subsequently filtered off. The filter cake was washed three times with acetone. The polymer obtained in this way was dried at 70° C. under reduced pressure (0.2 bar) for 15 hours.

This gave 6.9 g of colorless polymer which had a glass transition temperature of 101° C., a viscosity number of 507

TABLE 2

| Ex. | Monomer solution [% by weight of norbornene] | Amount of catalyst [mg] | Yield [g] | Tg [° C.] | VN [ml/g] | Mw [g/mol] | Mw/Mn |
| --- | --- | --- | --- | --- | --- | --- | --- |
| 6 | 50 | 5.4 | 32 | 79 | 97 | 59,000 | 1.7 |
| 7 | 30 | 4.3 | 49 | 55 | 103 | 56,000 | 1.6 |

Example 8

400 cm$^3$ of an 85% strength by weight solution of norbornene in toluene are placed in a 1 dm$^3$ autoclave which has previously been purged thoroughly with ethene. The solution was saturated with ethene by multiple pressurization with ethene (3.4 bar). 1 cm$^3$ of methylaluminoxane solution in toluene (10% strength by weight methylaluminoxane solution having a molar mass of 1300 g/mol according to cryoscopic determination) was metered in countercurrent into the reactor which had been prepared in this way and the mixture was stirred for 30 minutes at 70° C. A solution of 0.29 mg of (t-butylamido)dimethyl(tetramethyl-$\eta^5$-cyclopentadienyl)silanetitanium dichloride in 1 cm$^3$ of methylaluminoxane solution in toluene was added after preactivation for 15 minutes.

While stirring (800 rpm), polymerization was carried out for 65 minutes, with the ethene pressure being maintained at 3.4 bar by metering in further amounts.

After the end of the reaction time, the polymerization mixture was drained into a vessel and immediately introduced into 5 dm$^3$ of acetone, stirred for 10 minutes and the precipitated product was subsequently filtered off. The filter cake was washed three times with acetone. The polymer obtained in this way was dried at 70° C. under reduced pressure (0.2 bar) for 15 hours. This gave 1.6 g of colorless polymer which had a glass transition temperature of 121° C., a viscosity number of 255 ml/g, a weight average molar mass of 313,000 g/mol and a polydispersity of 2.5.

Example 9

400 cm$^3$ of an 85% strength by weight solution of norbornene in toluene were placed in a 1 dm$^3$ autoclave ml/g, a weight average molar mass of 609,000 g/mol and a polydispersity of 2.3.

Examples 10 to 16

400 cm$^3$ of an 85% strength by weight solution of norbornene in toluene were placed in a 1 dm$^3$ autoclave which had previously been purged thoroughly with ethene. The solution was saturated with ethene by multiple pressurization with ethene. 1 cm$^3$ of methylaluminoxane solution in toluene (10% strength by weight methylaluminoxane solution having a molar mass of 1300 g/mol according to cryoscopic determination) was metered in countercurrent into the reactor which had been prepared in this way and the mixture was stirred for 30 minutes at 70° C. A solution of 0.29 mg of (t-butylamido)dimethyl(tetramethyl-$\eta^5$-cyclopentadienyl)silanetitanium dichloride in 1 cm$^3$ of methylaluminoxane solution in toluene was added after preactivation for 15 minutes.

While stirring (800 rpm), polymerization was carried out for 1 hour, with the ethene pressure being maintained by metering in further amounts.

After the end of the reaction time, the polymerization mixture was drained into a vessel and immediately introduced into 5 dm$^3$ of acetone, stirred for 10 minutes and the precipitated product was subsequently filtered off. The filter cake was washed three times with acetone. The polymer obtained in this way was dried at 70° C. under reduced pressure (0.2 bar) for 15 hours.

This gave a colorless polymer. The corresponding reaction conditions and yields and also the characteristic data of the polymers obtained, e.g. glass transition temperatures, viscosity numbers, weight average molar masses and polydispersities are shown in Table 3 below.

TABLE 3

| Ex. | Ethene pressure [bar] | Polymerization time [min] | Yield [g] | Tg [° C.] | VN [ml/g] | $M_w$ [g/mol] | $M_w/M_n$ |
|---|---|---|---|---|---|---|---|
| 10 | 20.5 | 8 | 8.0 | 54 | — | 810,000 | 2.1 |
| 11 | 11.0 | 40 | 6.5 | 68 | 434 | 671,000 | 2.1 |
| 12 | 15.1 | 10 | 5.3 | 55 | 542 | 733,000 | 1.8 |
| 13 | 26.8 | 7 | 13.4 | 41 | — | 850,000 | 2.0 |
| 14 | 30.8 | 7 | 13.5 | 34 | — | 819,000 | 1.7 |
| 15 | 39.2 | 4 | 20.4 | 21 | — | 1,547,000 | 2.0 |
| 16 | 50.0 | 15 | 1.7 | 11 | — | 1,384,000 | 1.9 |

Example 17

400 cm³ of a 42% strength by weight solution of norbornene in toluene were placed in a 1 dm³ autoclave which had previously been purged thoroughly with ethene. The solution was saturated with ethene by multiple pressurization with ethene (44.8 bar). 1 cm³ of methylaluminoxane solution in toluene (10% strength by weight methylaluminoxane solution having a molar mass of 1300 g/mol according to cryoscopic determination) was metered in countercurrent into the reactor which had been prepared in this way and the mixture was stirred for 30 minutes at 70° C. A solution of 0.15 mg of (t-butylamido)dimethyl(tetramethyl-$\eta^5$-cyclopentadienyl)silanetitanium dichloride in 1 cm³ of methylaluminoxane solution in toluene was added after preactivation for 15 minutes.

While stirring (800 rpm), polymerization was carried out for six minutes, with the ethene pressure being maintained at 44.8 bar by metering in further amounts.

After the end of the reaction time, the polymerization mixture was drained into a vessel and immediately introduced into 5 dm³ of acetone, stirred for 10 minutes and the precipitated product was subsequently filtered off. The filter cake was washed three times with acetone. The polymer obtained in this way was dried at 70° C. under reduced pressure (0.2 bar) for 15 hours.

This gave 10.3 g of colorless polymer which had a glass transition temperature of −2° C., a weight average molar mass of 1,420,000 g/mol and a polydispersity of 1.9.

Comparative example 1

1000 cm³ of an 85% strength by weight solution of norbornene in toluene were placed in a 1.5 dm³ autoclave which had previously been purged thoroughly with ethene. The solution was saturated with ethene by multiple pressurization with ethene (6 bar). 20 cm³ of methylaluminoxane solution in toluene (10% strength by weight methylaluminoxane solution having a molar mass of 1300 g/mol according to cryoscopic determination) were metered in countercurrent into the reactor which had been prepared in this way and the mixture was stirred for 30 minutes at 70° C. A solution of 48 mg of dimethylsilylbis(cyclopentadienyl) zirconium dichloride in 20 cm³ of methylaluminoxane solution in toluene was added after preactivation for 15 minutes.

While stirring (750 rpm), polymerization was carried out for one hour, with the ethene pressure being maintained at 6 bar by metering in further amounts.

After the end of the reaction time, the polymerization mixture was drained into a vessel and immediately introduced into 5 dm³ of acetone, stirred for 10 minutes and the precipitated product was subsequently filtered off. The filter cake was washed alternately with three portions each of 10% hydrochloric acid and acetone, the residue was slurried in acetone and filtered off again. The polymer which had been purified in this way was dried at 80° C. under reduced pressure (0.2 bar) for 15 hours.

This gave 104 g of colorless polymer which had a glass transition temperature of 214° C., a viscosity number of 27 ml/g, a weight average molar mass of 25,000 g/mol and a polydispersity of 2.0.

Comparative example 2

600 cm³ of an 85% strength by weight solution of norbornene in toluene were placed in a 1.5 dm³ autoclave which had previously been purged thoroughly with ethene. The solution was saturated with ethene by multiple pressurization with ethene (16 bar). 20 cm³ of methylaluminoxane solution in toluene (10% strength by weight methylaluminoxane solution having a molar mass of 1300 g/mol according to cryoscopic determination) were metered in countercurrent into the reactor which had been prepared in this way and the mixture was stirred for 30 minutes at 70° C. A solution of 4.6 mg of dimethylsilylbis(cyclopentadienyl) zirconium dichloride in 20 cm³ of methylaluminoxane solution in toluene was added after preactivation for 15 minutes.

While stirring (750 rpm), polymerization was carried out for one hour, with the ethene pressure being maintained at 16 bar by metering in further amounts.

After the end of the reaction time, the polymerization mixture was drained into a vessel and immediately introduced into 5 dm3 of acetone, stirred for 10 minutes and the precipitated product was subsequently filtered off. The filter cake was washed alternately with three portions each of 10% hydrochloric acid and acetone, the residue was slurried in acetone and filtered off again. The polymer which had been purified in this way was dried at 80° C. under reduced pressure (0.2 bar) for 15 hours.

This gave 49 g of colorless polymer which had a glass transition temperature of 177° C., a viscosity number of 56 ml/g, a weight average molar mass of 47,000 g/mol and a polydispersity of 2.0.

Comparative examples 3 and 4

600 cm³ of an 85% strength by weight solution of norbornene in toluene were placed in a 1.5 dm³ autoclave which had previously been purged thoroughly with ethene. The solution was saturated with ethene by multiple pressurization with ethene. 10 cm³ of methylaluminoxane solution in toluene (10% strength by weight methylaluminoxane solution having a molar mass of 1300 g/mol according to cryoscopic determination) were metered in countercurrent into the reactor which had been prepared in this way and the mixture was stirred for 30 minutes at 70° C. A solution of 1 mg of isopropylene(cyclopentadienyl)(1-indenyl)zirconium dichloride in 10 cm³ of methylaluminoxane solution in toluene was added after preactivation for 15 minutes.

While stirring (750 rpm), polymerization was carried out for one hour, with the ethene pressure being maintained by metering in further amounts.

After the end of the reaction time, the polymerization mixture was drained into a vessel and immediately introduced into 5 dm³ of acetone, stirred for 10 minutes and the precipitated product was subsequently filtered off. The filter cake was washed alternately with three portions each of 10% hydrochloric acid and acetone, the residue was slurried in acetone and filtered off again. The polymer which had been purified in this way was dried at 80° C. under reduced pressure (0.2 bar) for 15 hours.

This gave a colorless polymer. The further reaction conditions and the characteristic data of the polymer are summarized in Table 4.

TABLE 4

| Comp. Ex. | Monomer solution [% by weight of norbornene] | Ethylene pressure [bar] | Yield [g] | $T_g$ [° C.] | VN [ml/g] | $M_w$ [g/mol] | $M_w/M_n$ |
|---|---|---|---|---|---|---|---|
| 3 | 50 | 10 | 44 | 163 | 70 | 62,000 | 2.0 |
| 4 | 30 | 12 | 116 | 120 | 63 | 56,000 | 2.1 |

Comparative examples 5 to 7

A solution of norbornene in toluene was placed in a 70 dm$^3$ autoclave which had previously been purged thoroughly with ethene. The solution was saturated with ethene by multiple pressurization with ethene. 400 cm$^3$ of methylaluminoxane solution in toluene (10% strength by weight methylaluminoxane solution having a molar mass of 1300 g/mol according to cryoscopic determination) were metered in countercurrent into the reactor which had been prepared in this way and the mixture was stirred for 30 minutes at 70° C. After preactivation for 30 minutes, a solution of isopropylene(cyclopentadienyl)(1-indenyl)zirconium dichloride in 300 cm$^3$ of methylaluminoxane solution in toluene was added.

While stirring (750 rpm), polymerization was carried out for one hour, with the ethene pressure being maintained by metering in further amounts.

After the end of the reaction time, the polymerization mixture was drained into a vessel and immediately introduced into 300 dm$^3$ of acetone, stirred for 30 minutes and the precipitated product was subsequently filtered off.

The filter cake was washed alternately with three portions each of 10% hydrochloric acid and acetone, the residue was slurried in acetone and filtered off again. The polymer which had been purified in this way was dried at 80° C. under reduced pressure (0.2 bar) for 15 hours.

This gave a colorless polymer. The further reaction conditions and the characteristic data of the polymer are summarized in Tables 5 and 6.

TABLE 5

| Comp. Ex. | Monomer solution [% by weight of norbornene] | Volume of monomer solution [dm$^3$] | Amount of catalyst [mg] | Ethylene pressure [bar] |
|---|---|---|---|---|
| 5 | 60 | 30 | 100 | 20 |
| 6 | 40 | 50 | 160 | 22 |
| 7 | 40 | 32 | 100 | 20 |

TABLE 6

| Comp. Ex. | Yield | $T_g$ [° C.] | VN [ml/g] | $M_w$ [g/mol] | $M_w/M_n$ |
|---|---|---|---|---|---|
| 5 | 8 | 105 | 47 | 29,000 | 1.9 |
| 6 | 7.4 | 89 | 41 | 21,000 | 1.9 |
| 7 | 7 | 82 | 38 | 21,000 | 1.8 |

Comparative example 8

600 cm$^3$ of an 80% strength by weight solution of norbornene in toluene were placed in a 1.5 dm$^3$ autoclave which had previously been purged thoroughly with ethene. The solution was saturated with ethene by multiple pressurization with ethene (3 bar). 20 cm$^3$ of methylaluminoxane solution in toluene (10% strength by weight methylaluminoxane solution having a molar mass of 1300 g/mol according to cryoscopic determination) were metered in countercurrent into the reactor which had been prepared in this way and the mixture was stirred for 30 minutes at 70° C. A solution of 50 mg of isopropylene(3-methylcyclopentadienyl)(1-indenyl)zirconium dichloride in 20 cm$^3$ of methylaluminoxane solution in toluene was added after preactivation for 15 minutes.

While stirring (750 rpm), polymerization was carried out for one hour, with the ethene pressure being maintained at 3 bar by metering in further amounts.

After the end of the reaction time, the polymerization mixture was drained into a vessel and immediately introduced into 5 dm$^3$ of acetone, stirred for 10 minutes and the precipitated product was subsequently filtered off. The filter cake was washed alternately with three portions each of 10% hydrochloric acid and acetone, the residue was slurried in acetone and filtered off again. The polymer which had been purified in this way was dried at 80° C. under reduced pressure (0.2 bar) for 15 hours.

This gave 43 g of colorless polymer which had a glass transition temperature of 174° C. and a viscosity number of 73 ml/g.

After the end of the reaction time, the polymerization mixture was drained into a vessel and immediately introduced into 5 dm$^3$ of acetone, stirred for 10 minutes and the precipitated product was subsequently filtered off. The filter cake was washed alternately with three portions each of 10% hydrochloric acid and acetone, the residue was slurried in acetone and filtered off again. The polymer which had been purified in this way was dried at 80° C. under reduced pressure (0.2 bar) for 15 hours.

This gave 43 g of colorless polymer which had a glass transition temperature of 174° C. and a viscosity number of 73 ml/g.

Comparative examples 9 to 12

A solution of 600 cm$^3$ of norbornene in toluene are placed in a 1.5 dm$^3$ autoclave which has previously been purged thoroughly with ethene. The solution was saturated with ethene (6 bar) by multiple pressurization with ethene. 20 cm$^3$ of methylaluminoxane solution in toluene (10% strength by weight methylaluminoxane solution having a molar mass of 1300 g/mol according to cryoscopic determination) were metered in countercurrent into the reactor which had been prepared in this way and the mixture was stirred for 30 minutes at 70° C. A solution of dimethylsilylbis(1-indenyl)zirconium dichloride in 20 cm3 of methylaluminoxane solution in toluene was added after preactivation for 15 minutes.

While stirring (750 rpm), polymerization was carried out for one hour, with the ethene pressure being maintained at 6 bar by metering in further amounts.

After the end of the reaction time, the polymerization mixture was drained into a vessel and immediately introduced into 5 dm³ of acetone, stirred for 10 minutes and the precipitated product was subsequently filtered off. The filter cake was washed alternately with three portions each of 10% hydrochloric acid and acetone, the residue was slurried in acetone and filtered off again. The polymer which had been purified in this way was dried at 80° C. under reduced pressure (0.2 bar) for 15 hours.

This gave a colorless polymer. The further reaction conditions and the characteristic data of the polymer are summarized in Table 7.

TABLE 7

| Comp. Ex. | Monomer solution [% by weight of norbornene] | Amount of catalyst [mg] | Yield [g] | Tg [° C.] | Tm [° C.] | VN [ml/g] |
|---|---|---|---|---|---|---|
| 9 | 85 | 5 | 21 | 122 | 122 | 45 |
| 10 | 85 | 5 | 20 | 178 | 118 | 65 |
| 11 | 80 | 0.5 | 2.5 | 138 | 120 | 45 |
| 12 | 30 | 60 | 180 | 103 | 115 | 86 |

Comparative examples 13 to 16

A solution of 600 cm³ of norbornene in toluene was placed in a 1.5 dm³ autoclave which had previously been purged thoroughly with ethene. The solution was saturated with ethene by multiple pressurization with ethene. 10 cm³ of methylaluminoxane solution in toluene (10% strength by weight methylaluminoxane solution having a molar mass of 1300 g/mol according to cryoscopic determination) were metered in countercurrent into the reactor which had been prepared in this way and the mixture was stirred for 30 minutes at 70° C. A solution of 8 mg of dimethylsilyl (cyclopentadienyl)(1-indenyl)zirconium dichloride in 10 cm³ of methylaluminoxane solution in toluene was added after preactivation for 15 minutes.

While stirring (750 rpm), polymerization was carried out for one hour, with the ethene pressure being maintained by metering in further amounts.

After the end of the reaction time, the polymerization mixture was drained into a vessel and immediately introduced into 5 dm³ of acetone, stirred for 10 minutes and the precipitated product was subsequently filtered off. The filter cake was washed alternately with three portions each of 10% hydrochloric acid and acetone, the residue was slurried in acetone and filtered off again. The polymer which had been purified in this way was dried at 80° C. under reduced pressure (0.2 bar) for 15 hours.

This gave a colorless polymer. The further reaction conditions and the characteristic data of the polymer are summarized in Table 8.

TABLE 8

| Comp. Ex. | Monomer solution (% by weight of norbornene) | Ethylene pressure [bar] | Yield [g] | Tg [° C.] | VN [ml/g] |
|---|---|---|---|---|---|
| 13 | 85 | 6 | 9.4 | 214 | 68 |
| 14 | 85 | 18 | 14.6 | 161 | 130 |
| 15 | 50 | 18 | 33.9 | 113 | 132 |
| 16 | 30 | 18 | 46.8 | 68 | 130 |

What is claimed is:

1. A process for preparing a cycloolefin copolymer by polymerization of from 0.1 to 99.9% by weight, based on the total amount of monomers, of at least one polycyclic olefin, from 0 to 99.9% by weight, based on the total amount of monomers, of at least one monocyclic olefin and from 0.1 to 99.9% by weight, based on the total amount of monomers, of at least one acyclic 1-olefin in the presence of a catalyst system comprising at least one cocatalyst and at least one metal complex having a strained geometry of the formula (I)

wherein
- $M^1$ is a metal of groups 3 to 10 or of the lanthanide series of the Periodic Table of the Elements,
- $R^1$ is a delocalized acyclic π system which optionally contains up to 5 hetero atoms, or an unsubstituted or substituted delocalized $C_5$–$C_{40}$-cyclic π system which optionally contains up to 5 hetero atoms,
- $R^2$ is a single- or multi-membered bridge which links the radicals $R^1$ and $R^3$ and comprises at least one atom of group 14 of the Periodic Table of the Elements or at least one boron atom and optionally comprise one or more sulfur or oxygen atoms and can form a fused ring system together with $R^1$,
- $R^3$ is an anionic or nonionic ligand which is coordinated to $M^1$ and comprises one or more nitrogen, phosphorus, oxygen and/or sulfur atoms and can form a fused ring system together with $R^2$, and
- $R^4$ is an anionic or nonionic ligand,
- n is 0,1,2,3, or 4 depending on the valence of M, and wherein the metal complex prior to use in the polymerization reaction is preactivated with the cocatalyst.

2. The process as claimed in claim 1, wherein the metal complex is a compound selected from the group consisting of (t-butylamido)(tetramethyl-η⁵-cyclopentadienyl) dimethylsilanetitanium dichloride,
(phenylamido)(tetramethyl-η⁵-cyclopentadienyl) dimethylsilanetitanium dichloride,
(cyclohexylamido)(tetramethyl-η⁵-cyclopentadienyl) dimethylsilanetitanium dichloride,
(t-butylamido)(1-η⁵-indenyl)dimethylsilanetitanium dichloride, (phenylamido)(1-η⁵-indenyl)dimethylsilanetitanium dichloride, (cyclohexylamido)(1-η⁵-indenyl)dimethylsilanetitanium dichloride, (t-butylamido)(9-η⁵-fluorenyl)dimethylsilanetitanium dichloride, (phenylamido)(9-η⁵-fluorenyl)dimethylsilanetitanium dichloride and (cyclohexylamido)(9-η⁵-fluorenyl) dimethylsilanetitanium dichloride.

3. The process as claimed in claim 2, wherein the cocatalyst is an aluminoxane.

4. The process as claimed in claim 1, which comprises polymerizing from 0.1 to 99.9% by weight, based on the total amount of monomers, of at least one polycyclic olefin of the formula III, IV, V, VI, VII or VII:

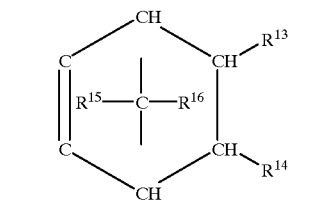
(III)

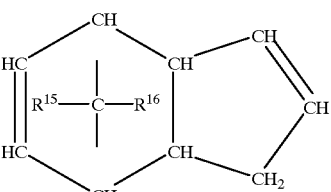
(IV)

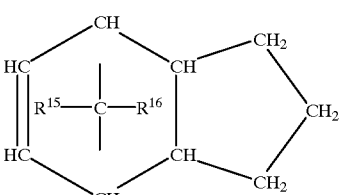
(IV)

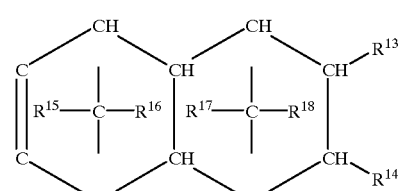
(V)

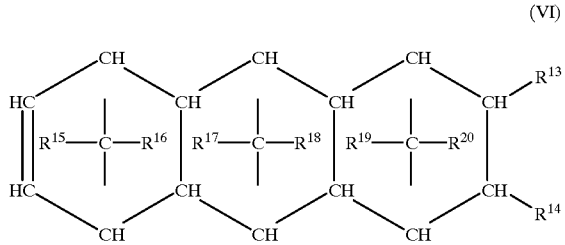
(VI)

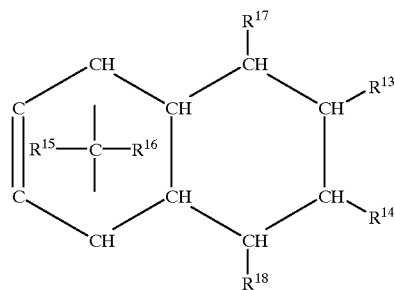
(VII)

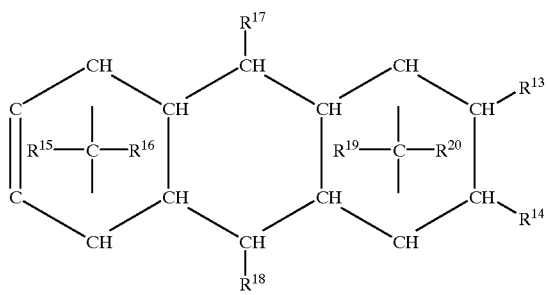
(VIII)

where $R^{13}$, $R^{14}$, $R^{15}$, $R^{16}$, $R^{17}$, $R^{18}$, $R^{19}$, and $R^{20}$ are identical or different and are each a hydrogen atom or a hydrocarbon radical, where identically numbered radicals in the various formulae can have different meanings, from 0–99.9% by weight, based on the total amount of monomers, of at least one monocyclic olefin of the formula IX

(IX)

where q is from 2 to 10, and from 0.1 to 99.9% by weight, based on the total amount of monomers are of at least one acyclic 1-olefin of the formula X

(X)

where $R^{21}$, $R^{22}$, $R^{23}$ and $R^{24}$ are identical or different and are each a hydrogen atom or a hydrocarbon radical.

5. The process as claimed in claim 4, wherein the polycyclic olefin is a compound of the formula III or V in which $R^{13}$, $R^{14}$, $R^{15}$, $R^{16}$, $R^{17}$, $R^{18}$, $R^{19}$, and $R^{20}$ are identical or different and are each a hydrogen atom or a hydrocarbon radical, where identically numbered radicals in the various formulae can have different meanings.

6. The process as claimed in claim 4, wherein the polycyclic olefin is norbornene or tetracyclododecane.

7. The process as claimed in claim 4, wherein the acyclic 1-olefin is ethylene.

8. The process as claimed in claim 4, wherein the cycloolefin copolymer prepared comprises at least 5 mol % of units derived from the cycloolefin.

9. The process as claimed in claim 4, wherein the cycloolefin copolymer prepared consists of units derived from monomers which have, apart from the olefinic double bond required for the polymerization, no further unsaturated functionalities.

10. The process as claimed in claim 4, wherein a temperature of from −78 to 150° C. and a pressure of from 0.01 to 64 bar are employed.

11. The process as claimed in claim 4, wherein a temperature of from 0 to 100° C. and a pressure of from 0.01 to 64 bar are employed.

12. The process as claimed in claim 4, wherein the polymerization is carried out in a liquid cycloolefin or in a cycloolefin solution.

13. A cycloolefin copolymer obtained by the process as claimed in claim 1.

14. The process as claimed in claim 1, wherein $R^6$ are identical or different and are each a hydrogen atom, a halogen atom, a $C_1$–$C_{10}$-alkyl group, which may be halogenated, a $C_6$–$C_{20}$-aryl group, which may be halogenated, a $C_6$–$C_{20}$-aryloxy group, a $C_2$–$C_{12}$-alkenyl group, a $C_7$–$C_{40}$-arylalkyl group, a $C_8$–$C_{40}$-arylalkenyl group, —$SiR^7_3$, $NR^7_2$, —$Si(OR^7)_3$, —$Si(SR^7)_3$ or —$PR^7_2$,
  $R^8$ is a hydrogen atom, a halogen atom, a $C_1$–$C_8$-alkyl group, which may be halogenated, a $C_6$–$C_{20}$-aryl group, which may be halogenated, a $C_6$–$C_{20}$-aryloxy group, a $C_2$–$C_{12}$-alkenyl group, a $C_7$–$C_{40}$-arylalkyl group, a $C_7$–$C_{40}$-alkylaryl group, a $C_8$–$C_{40}$-arylalkenyl group, a —$SiR^9_3$, —$NR^9_2$, —$Si(OR^9)_3$, —$Si(SR^9)_3$ or —$PR^9_2$,
  $R^4$ are identical or different and each are a hydrogen atom, a $C_1$–$C_{10}$-alkyl group, a $C_1$–$C_{10}$-alkoxy group, a $C_6$–$C_{10}$-aryl group, a $C_6$–$C_{25}$-aryloxy group, a $C_2$–$C_{10}$-alkenyl group, a $C_7$–$C_{40}$-arylalkyl group or a $C_7$–$C_{40}$-arylalkenyl group, an OH group, a halogen atom or $NR^{10}_2$,
  $R^5$ are identical or different and are each a hydrogen group, a halogen group, a $C_1$–$C_{10}$-alkyl group, which may be halogenated, a $C_6$–$C_{20}$-aryl group which may be halogenated, a $C_6$–$C_{20}$-aryloxy group, a $C_2$–$C_{12}$-alkenyl group, a $C_7$–$C_{40}$-arylalkyl group, a $C_7$–$C_{40}$-alkylaryl group or a $C_8$–$C_{40}$-arylalkenyl group, —$SiR^{11}_3$, —$NR^{11}_2$, —$Si(OR^{11})_3$—$PR^{11}_2$ or two or more adjacent substituents $R^5$ together with the atoms connecting them form a ring system which comprises six to twenty carbon atoms.

15. The process as claimed in claim 1, wherein $R^6$ is identical or different and are each a hydrogen atom, a $C_1$–$C_{10}$-alkyl group which may be halogenated, a $C_6$–$C_{20}$-aryl group, which may be halogenated, a $C_6$–$C_{20}$-aryloxy group, a $C_2$–$C_{12}$-alkenyl group, a $C_7$–$C_{40}$-arylalkyl group, a $C_7$–$C_{40}$-alkylaryl group or a $C_8$–$C_{40}$-arylalkenyl group,
  $R^8$ is a hydrogen atom, a $C_1$–$C_8$-alkyl group, which may be halogenated, a $C_1$–$C_{10}$-alkoxy group, a $C_6$–$C_{20}$-aryl group which may be halogenated, a $C_6$–$C_{20}$-arloxy group, a $C_2$–$C_{12}$-alkenyl group, a $C_7$–$C_{40}$-arylalkyl group, a $C_7$–$C_{40}$alkylaryl group or a $C_8$–$C_{40}$-arylalkenyl group,
  $R^4$ are identical or different and are each a hydrogen atom, a $C_1$–$C_{10}$-alkyl group, a $C_1$–$C_{10}$-alkoxy group, a $C_6$–$C_{10}$-aryl group, a $C_6$–$C_{25}$-aryloxy group, a $C_2$–$C_{10}$-alkenyl group, a $C_7$–$C_{40}$-arylalkyl group, a $C_7$–$C_{40}$-arylalkenyl group an OH group, a halogen atom or $NR^{10}_2$.

16. The process as claimed in claim 4, wherein $R^{21}$, $R^{22}$ and $R^{24}$ are identical or different and each a hydrogen atom or a $C_6$–$C_{10}$-aryl radical or a $C_1$–$C_8$-alkyl radical.

17. The process as claimed in claim 1, wherein said at least one metal complex is of the formula (Ia)

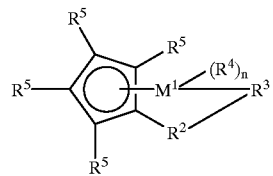

(Ia)

wherein
  $M^1$ is a metal of group 4 or of the lanthanide series of the Periodic Table of the Elements,
  $R^2$ is a single- or multi-numbered bridge which links the $\eta^5$-coordinated cyclic $\pi$ system and is

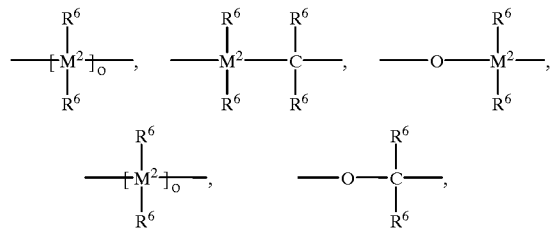

=$BR^6$, =$AIR6$, —Ge—, —Sn—, —O—, —S—, =SO, =$SO_2$, =$NR^6$, =CO, =$PR^6$ or =$P(O)R^6$, where $R^6$ are identical or different and are each a hydrogen atom, a halogen atom, a $C_1$–$C_{40}$-group which may be halogenated, —$SiR^7_3$, —$NR^7_2$, —$Si(OR^7)_3$, —$Si(SR^7)_3$, or —$PR^7_2$, where $R^7$ are identical each a halogen atom, a $C_1$–$C_{10}$-alkyl group or a $C_6$–$C_{10}$-aryl group or form a ring system, where o>1, and
  $M^2$ is silicon, germanium or tin,
  $R^3$ is O, S, $NR^8$, $PR^8$ or an uncharged 2-electron donor ligand selected from the group consisting of $OR^8$, $SR^8$, $NR^8_2$ and $PR^8_2$ where $R^8$ is a hydrogen atom, a halogen atom, $C_1$–$C_{40}$-group which may be halogenated, —$SiR^9_3$, —$NR^9_2$, —$Si(OR^9)_3$, —$Si(SR^9)_3$ or —$PR^9_2$, where $R^9$ identical or different and are each a halogen atom, a $C_1$–$C_8$-alkyl group or a $C_6$–$C_{10}$-aryl group,
  $R^4$ are identical or different and are each a hydrogen atom, a $C_1$–$C_{40}$-group an OH group, a halogen atom or $NR^{10}_2$, where $R^1$ is a halogen atom, a $C_1$–$C_{10}$-alkyl group or a $C_6$–$C_{10}$-aryl group, or $R^4$ together with the atoms connecting them form a ring system, where n=1 or 2,
  $R^5$ are identical or different and are each a hydrogen atom, a halogen atom, a $C_1$–$C_{40}$-group which may be halogenated, —$SiR^{11}_3$, —$NR^{11}_2$, —$Si(OR^{11})_3$, —$Si(SR^{11})_3$ or —$PR^{11}_2$, where $R^{11}$ are identical or different and are each a halogen atom, a $C_1$–$C_{10}$-alkyl group or a $C_6$–$C_{10}$-aryl group or form a ring system, or two or more adjacent substituents $R^5$ together with the atoms connecting them form a ring system.

18. The process as claimed in claim 17, wherein $R^6$ are identical and $R^3$ is $OR^8$, $SR^8$, and $PR^8_2$ where $R^8$ is a hydrogen atom, a halogen atom, $C_1$–$C_{40}$-group which may be halogenated, —$SiR^9_3$, —$NR^9_2$, —$Si(OR^9)_3$, —$Si(SR^9)_3$ or —$PR^9_2$, where $R^9$ are identical or different and are each a halogen atom, a $C_1$–$C_8$-alkyl group or a $C_6$–$C_{10}$-aryl group.

19. A process for preparing a cycloolefin copolymer by polymerization of from 0.1 to 99.9% by weight, based on the total amount of monomers, of at least one polycyclic olefin, from 0 to 99.9% by weight, based on the total amount of monomers, of at least one monocyclic olefin and from 0.1 to 99.9% by weight, based on the total amount of monomers, of at least one acyclic 1-olefin in the presence of a catalyst system comprising at least one cocatalyst and at least one metal complex having a strained geometry and is of the formula (Ia)

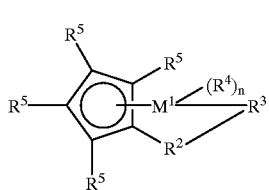

(Ia)

wherein $M^1$ is a metal of groups 3 to 10 or the lanthenide series of the Periodic Table of the Elements, $R^2$ is a single- or multi-numbered bridge which links the $\eta^5$-coordinated cyclic $\pi$ system and is

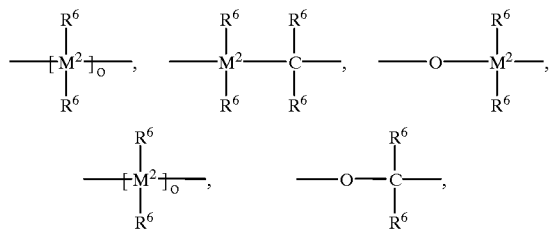

=$BR^6$, =$AlR6$, —Ge—, —Sn—, —O—, —S—, =SO, =$SO_2$, =$NR^6$, =CO, =$PR^6$ or =$P(O)R^6$, where $R^6$ are identical or different and are each a hydrogen atom, a halogen atom, a $C_1$–$C_{40}$-group which may be halogenated, —$SiR^7_3$, —$NR^7_2$, —$Si(OR^7)_3$, —$Si(SR^7)_3$, or —$PR^7_2$, where $R^7$ are identical or different and are each a halogen atom, a $C_1$–$C_{10}$-alkyl group or a $C_6$–$C_{10}$-aryl group or form a ring system, where o>1, and $M^2$ is silicon, germanium or tin, $R^3$ is O, S, $NR^8$, $PR^8$ or an uncharged 2-electron donor ligand selected from the group consisting of $OR^8$, $SR^8$, $NR^8_2$ and $PR^8_2$ where $R^8$ is a hydrogen atom, a halogen atom, $C_1$–$C_{40}$-group which may be halogenated, —$SiR^9_3$, —$NR92$, —$Si(OR^9)_3$, —$Si(SR^9)_3$ or —$PR^9_2$, where $R^9$ are identical or different and are each a halogen atom, a $C_1$–$C_8$-alkyl group or a $C_6$–$C_{10}$-aryl group, $R^4$ are identical or different and are each a hydrogen atom, a $C_1$–$C_{40}$-group an OH group, a halogen atom or $NR^{10}_2$, where $R^{10}$ is a halogen atom, a $C_1$–$C_{10}$-alkyl group or a $C_6$–$C_{10}$-aryl group, or $R^4$ together with the atoms connecting them form a ring system, where n=1 or 2, $R^5$ are identical or different and are each a hydrogen atom, a halogen atom, a $C_1$–$C_{40}$-group which may be halogenated, —$SiR^{11}_3$, —$NR^{11}_2$, —$Si(OR^{1)}_3$, —$Si(SR^{11})_3$ or —$PR^{11}_2$, where $R^{11}$ are identical or different and are each a halogen atom, a $C_1$–$C_{10}$-alkyl group or a $C_6$–$C_{10}$-aryl group or form a ring system, or two or more adjacent substituents $R^5$ together with the atoms connecting them form a ring system and wherein at least one $R^5$ is hydrogen and wherein the metal complex prior to use in the polymerization reaction is preactivated with the cocatalyst.

20. The process as claimed in claim 1, wherein the preactivation occurs at a time from 5 to 60 minutes.

21. The process as claimed in claim 1, wherein $R^1$ is $C_4$–$C_{20}$-alkenyl, $C_4$–$C_{20}$-alkynyl, $C_3$–$C_{20}$- allyl, $C_4$–$C_{20}$-alkadienyl or $C_4$–$C_{20}$-polyenyl.

22. A process for preparing a cycloolefin copolymer by polymerization of from 0.1 to 99.9% by weight, based on the total amount of monomers, of at least one polycyclic olefin, from 0 to 99.9% by weight, based on the total amount of monomers, of at least one monocyclic olefin and from 0.1 to 99.9% by weight, based on the total amount of monomers, of at least one acyclic 1-olefin in the presence of a catalyst system comprising at least one cocatalyst and at least one metal complex having a strained geometry of the formula (I)

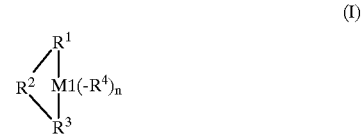

(I)

wherein $M^1$ is titanium, zirconium, or of the lanthanide series of the Periodic Table of the Elements, $R^1$ is a delocalized acyclic $\pi$ system which optionally contains up to 5 hetero atoms, or an unsubstituted or substituted delocalized $C_5$–$C_{40}$-cyclic $\pi$ system which optionally contains up to 5 hetero atoms, $R^2$ is a single- or multi-membered bridge which links the radicals $R^1$ and $R^3$ and comprises at least one atom of group 14 of the Periodic Table of the Elements or at least one boron atom and optionally comprise one or more sulfur or oxygen atoms and optionally form a fused ring system together with $R^2$, $R^3$ is an anionic or nonionic ligand which is coordinated to $M^1$ and comprises one or more nitrogen, phosphorus, oxygen and/or sulfur atoms and can form a fused ring system together with $R^2$, and $R^4$ is an anionic or nonionic ligand, n is 0,1,2,3, or 4 depending on the valence of M, and wherein the metal complex prior to use in the polymerization reaction is preactivated with the cocatalyst.

23. The process as claimed in claim 1, wherein the metal complex is a compound of the formula (Ia)

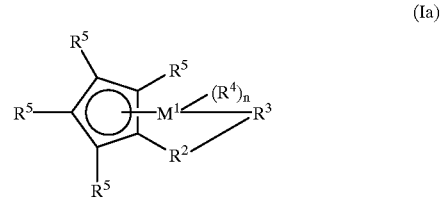

(Ia)

wherein $M^1$ is titanium, $R^2$ is a single-, two- or three-membered bridge which links the $\eta^5$-coordinated cyclic $\pi$ system and is

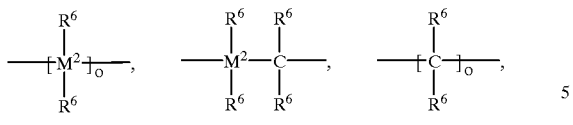

where $R^6$ are identical or different and are each a hydrogen atom, a $C_1$–$C_{40}$-group which may be halogenated, wherein o=1, 2 or 3, $M^2$ is silicon, $R^3$ is $NR^8$, where $R^8$ is a hydrogen atom, a $C_1$–$C_{40}$-group which may be halogenated, $R^4$ are identical or different and are each a hydrogen atom, a $C_1$–$C_{40}$-group an OH group, a halogen atom or $NR^{10}{}_2$, where $R^{10}$ is a halogen atom, a $C_1$–$C_{10}$-alkyl group or a $C_6$–$C_{10}$-aryl group, or together with the atoms connecting them form a ring system, $R^5$ are identical or different and are each a hydrogen atom, a $C_1$–$C_{10}$-alkyl group or trimethylsilyl group or two of the substituents $R^5$ together with cyclopentadienyl system connecting them form a six-membered aromatic fused ring.

24. A process for preparing a cycloolefin copolymer by polymerization of from 0.1 to 99.9% by weight, based on the total amount of monomers, of at least one polycyclic olefin, from 0 to 99.9% by weight, based on the total amount of monomers, of at least one monocyclic olefin and from 0.1 to 99.9% by weight, based on the total amount of monomers, of at least one acyclic 1-olefin in the presence of a catalyst system comprising at least one cocatalyst and at least one metal complex having a strained geometry of the formula (I)

wherein $M^1$ is a metal of groups 3 to 10 or of the lanthanide series of the Periodic Table of the Elements, $R^1$ is a delocalized acyclic π system which optionally contains up to 5 hetero atoms, or an unsubstituted or substituted delocalized $C_5$–$C_{40}$-cyclic π system which optionally contains up to 5 hetero atoms, $R^2$ is a single- or multi-membered bridge which links the radicals $R^1$ and $R^3$ and comprises at least one atom of group 14 of the Periodic Table of the Elements or at least one boron atom and optionally comprise one or more sulfur or oxygen atoms and optionally form a fused ring system together with $R^1$, $R^3$ is an anionic or nonionic ligand which is coordinated to $M^1$ and comprises one or more nitrogen, phosphorus, oxygen and/or sulfur atoms and can form a fused ring system together with $R^2$, and $R^4$ is identical or different and is each a hydrogen atom, a $C_2$–$C_{40}$-group an OH group, a halogen atom or $NR^{10}{}_2$, where $R^{10}$ is a halogen atom, a $C_1$–$C_{10}$-alkyl group or a $C_6$–$C_{10}$-aryl group, or $R^4$ together with the atoms connecting them form a ring system, n is 0,1,2,3, or 4 depending on the valence of M, and wherein the metal complex prior to use in the polymerization reaction is preactivated with the cocatalyst.

* * * * *

UNITED STATES PATENT AND TRADEMARK OFFICE
CERTIFICATE OF CORRECTION

PATENT NO. : 6,365,686 B1
DATED : April 2, 2002
INVENTOR(S) : Jacobs et al.

It is certified that error appears in the above-identified patent and that said Letters Patent is hereby corrected as shown below:

Column 40,
Line 33, after "identical" insert -- or different --.
Line 42, after "$R^9$" insert -- are --.
Line 46, delete "$R^1$" insert -- $R^{10}$ --.

Signed and Sealed this

Tenth Day of December, 2002

JAMES E. ROGAN
*Director of the United States Patent and Trademark Office*